(12) United States Patent
Busch et al.

(10) Patent No.: US 7,191,070 B2
(45) Date of Patent: Mar. 13, 2007

(54) METHODS FOR DETERMINING ENANTIOMERIC PURITY

(75) Inventors: Kenneth W. Busch, Waco, TX (US); Isabel Maya P. Swamidoss, TamiNadu (IN); Sayo Fakayode, Waco, TX (US); Marianna Busch, Waco, TX (US)

(73) Assignee: Baylor University, Waco, TX (US)

( * ) Notice: Subject to any disclaimer, the term of this patent is extended or adjusted under 35 U.S.C. 154(b) by 8 days.

(21) Appl. No.: 11/004,597

(22) Filed: Dec. 3, 2004

(65) Prior Publication Data

US 2005/0192767 A1 Sep. 1, 2005

Related U.S. Application Data

(60) Provisional application No. 60/526,494, filed on Dec. 3, 2003.

(51) Int. Cl.
*G01N 31/00* (2006.01)
(52) U.S. Cl. ............................... 702/22; 702/23
(58) Field of Classification Search ................ 702/22, 702/23
See application file for complete search history.

(56) References Cited

U.S. PATENT DOCUMENTS

| | | | |
|---|---|---|---|
| 5,989,916 A | 11/1999 | Purdie | |
| 6,922,645 B2 * | 7/2005 | Haaland et al. | 702/76 |
| 6,934,638 B2 * | 8/2005 | Ito et al. | 702/22 |
| 2002/0103232 A1 | 8/2002 | Whittle et al. | |

OTHER PUBLICATIONS

Balabai, et al., Orientational Dynamics of B-Cyclodextrin Inclusion Complexes, J. Phys. Chem. B 1998, 102, pp. 9617-9624.
Bortolus, et al., Chiral Discrimination of Camphorquinone Enantiomers by Cyclodextrins, J. Phys. Chem. A 2002, 106, pp. 1686-1694.
Cox, et al., Dialkylaminobenzonitriles as Fluorescence Polarity Probes for Aqueous Solutions . . . , J. Photochem. Photobiol. 1984, 39(5), pp. 597-601.
Dotsikas, et al., Interaction of 6-p-toluidinylnaphthalene-2-sulphonate with B-cyclodextrin, J. Pharm. Biomed. Anal. 2000, 23, pp. 997-1003.
Jiang, et al., Imtramolecular exciplex and cation-mediated charge-transfer fluorescence . . . , J. Chem. Soc., Perkin Trans. 2001, 2, pp. 1274-1279.
Martens, et al., Multivariate Calibration, 1989, John Wiley & Sons, Chichester, Great Britain.
Otagiri, et al., Inclusion complexes of B-Cyclodextrin with Tranquilizing Drugs Phenothiazines . . . , Chem. Pharm. Bull. 1975, 23, pp. 188-195.

(Continued)

*Primary Examiner*—John Barlow
*Assistant Examiner*—Stephen J. Cherry
(74) *Attorney, Agent, or Firm*—Jackson Walker L.L.P.

(57) ABSTRACT

A new strategy for the quantitative determination of enantiomeric purity that combines guest-host complexation, spectroscopy, and chemometric modeling. Spectral data for samples of known enantiomeric composition is subjected to a type of multivariate regression modeling known as partial least squares ("PLS-1") regression. The PLS-1 regression produces a mathematical model that can be used to predict the enantiomeric composition of a set of samples of unknown enantiomeric purity.

24 Claims, 22 Drawing Sheets

OTHER PUBLICATIONS

Schiller, et al., The Inclusion of Pyronine by B- and y-Cyclodextrin, J. Schem. Soc., Faraday Trans. 1987, 83(11), pp. 3237-3248.

Smith, et al., Spectroscopic Study of the Interaction of Catechin with a-, B-, and y-Cyclodextrins, J. Phys. Chem. 1994, 98, pp. 8627-8631.

Sullivan, G.R., Chiral Lanthanide Shift Reagents, Top. Stereochem. 1978, 10, pp. 287-329.

Suzuki, H., Electronic Absorption Spectra and Geometry of Organic Molecules, 1967, pp. 102-105, Academic Press, New York, NY.

Park, et al., Excited-State Proton Transfer of 2-Naphthol Inclusion Complexes with Cyclodextrins, J. Phys. Chem. 1994, 98, pp. 6158-6199.

Busch KW, Swamidoss IM, Fakayode SO, Busch MA. Determination of the enantiomeric composition of guest molecules by chemometric analysis of the UV-visible spectra of cyclodextrin guest-host complexes. J Am Chem Soc. Feb. 19, 2003; 125(7):1690-1

Haglund P. Enantioselective Separation of Polychlorinated Biphenyl Atropisomers Using Chiral High-Performance Liquid Chromatography. J of Chromatography A, Elsevier, Amsterdam, NL. Feb. 16, 1996;724(1):219-228.

Louka YL, Sabbah S, Scriba GK. Method development and validation for the chiral separation of peptides in the presence of cyclodextrins using capillary electrophoresis and experimental design. J Chromatogr A. Oct. 5, 2001;931(1-2):141-52.

Notification of Transmittal of the International Search Report and the Written Opinion of the International Searching Authority, or the Declaration from the PCT dated Jun. 1, 2006.

\* cited by examiner

METHODS FOR DETERMINING ENANTIOMERIC PURITY

This application claims priority to U.S. Provisional Patent Application, Ser. No. 60/526,494, entitled "METHODS FOR DETERMINING ENANTIOMERIC PURITY" filed on Dec. 03, 2003, having Kenneth W. Busch, Isabel M. Swamidoss, Sayo Fakayode, and Marianna Busch, listed as the inventor(s), the entire content of which is hereby incorporated by reference.

BACKGROUND

The work herein was supported in part by a grant from the Robert A. Welch Foundation.

This invention relates to a strategy for determining the enantiomeric purity of a compound through guest-host complexation, spectroscopy, particularly UV absorption spectroscopy and fluorescence spectroscopy, and chemometric modeling.

The need for improved strategies for the assessment of enantiomeric purity arises from increased pressure on the pharmaceutical industry by government agencies for documentation on the pharmacological effects of individual enantiomers and the simultaneous demand in drug development for determination of enantiomeric excess in large combinatorial libraries. While many analytical techniques for chiral analysis have been developed over the years, gas and liquid chromatography, capillary electrophoresis and nuclear magnetic resonance are currently the most widely used. For high throughput screening strategies, slow chromatographic methods are not attractive. Rapid spectroscopic techniques are the most desirable.

Experimental discrimination of enantiomers is carried out conventionally by means of chiral auxiliary agents such as chiral shift reagents, chiral complexing agents, and chiral solvents. (Sullivan, G.R., *Top. Stereochem.*, vol. 10, pp. 287–329, 1978). This diastereomeric discrimination arises when a given enantiomer of the chiral auxiliary interacts with two enantiomers of a compound to produce diastereomeric pairs with different physical properties as shown below in Scheme 1, where $R_{CA}$ is a chiral auxiliary.

Scheme 1

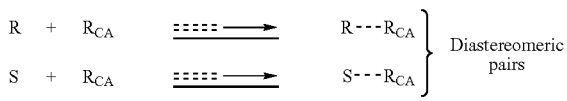

Chromogenic enantioselective chiral hosts are capable of discriminating between enantiomers of chiral guests through a change in the visible absorption spectrum of the enantioselective complex, i.e., through a color change. (Otagiri, et al., *Chem. Pharm. Bull.*, vol. 23, p. 188, 1975; Schiller, et al., *J. Chem. Soc., Faraday Trans.*, vol. 83, p. 3227, 1987; Park, et al., *J. Phys. Chem.*, vol. 98, p. 6158, 1994; Cox, et al., *J. Photochem. Photobiol.*, vol. 39, p. 597, 1984; Bortolus, et al., *J. Phys. Chem. A*, vol. 106, p. 1686, 2002; Balabai, *J. Phys. Chem.*, vol. 102, p. 9617, 1998). Under this strategy, the complexation of one enantiomer of a chiral substrate with a chiral host results in a visible spectral shift and/or the formation of an entirely new visible band, while little or no color change is observed when the other enantiomer complexes with the chiral host.

Traditonally, cyclodextrins are used as host molecules. Cyclodextrins ("CDs") are homochiral barrel-shaped sugar molecules that can form transient, non-covalent diastereomeric guest-host complexes with chiral guest molecules. Because the complexes that are formed are diastereomeric, they have different physical properties. Consequently, there are small changes in their spectra. (Suzuki, *Electronic Absorption Spectra and Geometry of Organic Molecules*, p. 102, 1967). These small spectral variations are often dismissed as having little utility for predicting the composition of a sample because the variations are small, the bands overlap, and the spectra do not appear to show a consistent trend (such as an offset) with composition. However, chemometric methods, such as multivariate regression, offer a variety of powerful techniques for revealing hidden relationships in data that are not immediately apparent.

Multivariate regression modeling ("MRM") is widely used in chemistry as a means of correlating spectral data with known compositional changes. (Martens, et al., *Multivariate Calibration*, 1989). While the use of chemometrics in near-infrared spectroscopy is well-established, its use in other spectral regions, such as the ultraviolet region, is not as common. MRM is used for the chemometric analysis of the spectral data of the solutions containing cyclodextrin guest-host inclusion complexes because the solution spectra are composite spectra, simultaneously containing contributions from complexed species (diastereomeric CD inclusion complexes) as well as uncomplexed species that are present because the complexation reaction is not complete.

SUMMARY

This invention relates to a new strategy for the quantitative determination of enantiomeric purity. The strategy combines guest-host complexation, spectroscopy, and chemometric modeling. In particular, a type of multivariate regression modeling known as partial least squares ("PLS-1") regression is used to develop a mathematical model that can be used to predict the enantiomeric composition of a set of samples.

Multivariate regression is widely known in many areas of chemistry and can serve as a particularly powerful computational tool for correlating spectral data with known compositional changes in a test set of samples. The basic objective of the method is to develop a mathematical model that relates two sets of variables to each other so that the independent or X-variables can be used to determine the dependent or Y-variable. In this case, the X-variables are the spectral information and the Y-variable is the enantiomeric composition.

To avoid problems with colinearity in the data, all multivariate regression techniques require an orthogonal basis set or coordinate system on which to represent the data. To achieve this condition, modem regression techniques employ projection methods to obtain a series of variance-scaled eigenvectors that can serve as a new coordinate system for the data. This form of data decomposition assures an orthogonal coordinate system for the data. At the same time, it provides a way to reduce the dimensionality of the data because only the major eigenvectors are needed to represent the data. Finally, when the data are represented on the new coordinate system, new insight is often gained as new relationships that were formerly obscured in the old coordinate system are revealed.

Compared with principal component regression, another well known method of MRM, the PLS-1 algorithm is especially powerful as a means of multivariate regression, because both the spectral data and the dependent variable (in this case, enantiomeric composition) are actively involved in the construction of the new basis set of variance-scaled eigenvectors that serve as PLS components. In this way, the PLS regression algorithm focuses on those aspects of the spectral data that are most important in predicting enantiomeric composition.

Broadly, one aspect of the present invention involves a method for determining an unknown enantiomeric composition of a chiral compound in an unknown sample, comprising the steps of:

(1) preparing a series of known samples, each of the known samples comprising a first complex, wherein, the first complex in each of the known samples comprises a ratio of a host compound and the chiral compound having a known enantiomeric composition, wherein in each of the known samples, the ratio of the chiral compound to the host compound remains the same and the enantiomeric composition of the chiral compound is varied, and wherein in each of the known samples, the concentrations of the chiral compound and of the host compound are at a fixed or preset level;

(2) collecting spectral data of the known samples at various wavelengths;

(3) performing a principal component analysis to select a spectral range of wavelengths in which the spectral differences arising in each of the known samples due to an influence of the enantiomeric composition is most appreciable to give the selected range of wavelengths;

(4) performing a partial-least-squares regression of the spectral data over the selected range of wavelengths for each of the series of the known samples to determine a series of regression coefficients;

(5) entering the series of regression coefficients for the selected range of wavelengths into a regression vector;

(6) collecting spectral data of the unknown sample at various wavelengths to give unknown spectral data, wherein the unknown sample comprises a second complex having the same ratio of the chiral compound to the host compound as that of the first complex in each of the known samples, and wherein the concentrations of the chiral compound and of the host compound are at the same fixed or preset level used in step #1; and (7) inserting the unknown spectral data into the regression vector to allow calculation of the unknown enantiomeric composition of the chiral compound in the unknown sample.

In the current invention, chemometric analysis of spectral data of solutions containing cyclodextrin guest-host inclusion complexes is used to determine the enantiomeric purity of simple chiral compounds. The spectral data may be collected using any wavelength light. Useful spectroscopic techniques include near IR, IR, and far IR; near UV, UV, and far UV; Raman; and NMR. NMR is routinely used in chiral analysis with shift reagents. However, combined with chemometics some shift reagents whose "shift" is small may be found useful. The most preferable spectroscopic techniques include absorption UV spectrometry, fluorescence emission spectrometry, Raman spectrometry, and NMR.

The method is quite general and can apply to a diversity of compounds. Depending on the guest molecule, different hosts (alpha, beta, or gamma-CD, as well as synthetically modified cyclodextrins) may give somewhat better results in terms of correlation coefficients and prediction ability with future samples. The host compound can be any homochiral molecule capable of forming a diastereomeric compound or complex with the chiral guest compound. Potential chiral hosts include modified cyclodextrins, chiral crown ethers (coronands), chiral cryptands, chiral podands, and chiral calixarenes, as well as naturally occurring homochiral molecules like starch (beta-amylose). Any homochiral molecule that can form a diastereomeric compound or complex with the guest molecule is useful. Because the method depends solely on the changes produced in the spectrum of the complexed guest molecule as a result of differences in the binding conditions for the different enantiomeric forms of the guest molecule with the chiral host, it does not assume or depend on any particular stoichiometry of the guest/host complex. Whatever guest/host complexes may be present in the solution are not expected to vary because the concentrations of the guest and the host are fixed.

DETAILED DESCRIPTION OF PREFERRED EMBODIMENTS

The current invention pertains to methods for determining enantiomeric purity of solutions of compounds whose enantiomeric composition is unknown. The methods involve guest-host complexation, spectroscopy, and chemometric modeling. A type of multivariate regression modeling known as partial least squares ("PLS-1") regression is used to develop a mathematical model that can be used to predict the enantiomeric composition of a set of samples.

For solutions containing a fixed concentration of chiral analyte and a fixed concentration of host compound, the UV absorption spectra vary slightly as the enantiomeric composition of the chiral guest molecule is changed. These small spectral changes can then be correlated with the known enantiomeric composition of a training set of samples using standard multivariate regression modeling (partial-least-squares regression, "PLS-1").

In addition to UV absorption spectrometry, fluorescence spectrometry can also be used. Fluorescence spectrometry offers several potential instrumental advantages when compared with absorption spectrophotometry. For example, it is well established, from a purely instrumental standpoint, that fluorescence measurements are more sensitive than absorption measurements because it is easier to detect a small emission signal over a low background than it is to distinguish the difference between two large intensities (I and I°) as in absorbance. In addition, since fluorescence is an emission technique, it is somewhat easier to implement in certain situations, because it is not necessary to monitor both the incident and the transmitted intensity as required for absorption measurements. Other preferable spectroscopic techniques include Raman spectrometry and NMR.

While purely instrumental factors may influence the sensitivity of detection of an analyte, it should be realized that with chiral analysis by multivariate regression modeling of spectral data, the question of sensitivity is not based solely on instrumental considerations. The spectral information that is actually used in regression modeling is encoded in the shape of the band envelope (and the extent to which this shape varies with enantiomeric composition) and not with detecting the intensity of the band maximum over a small background (i.e., the conventional detection limit).

Figure 1:
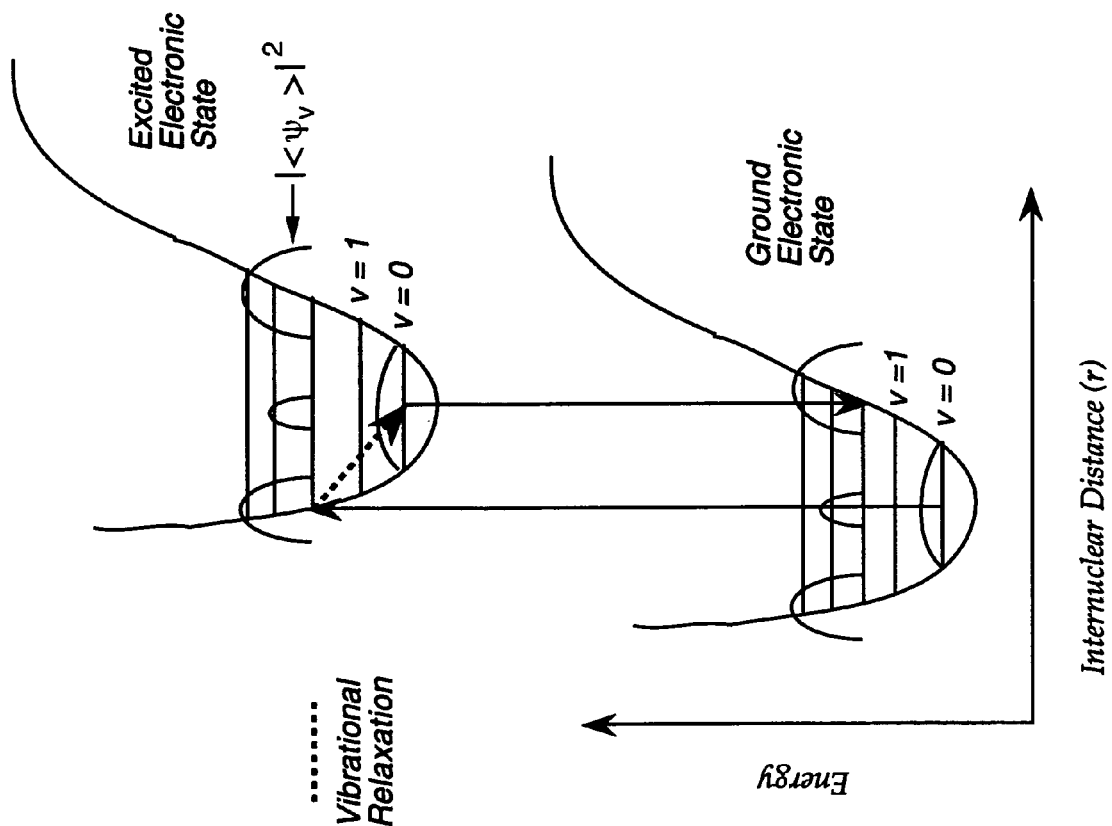
FIG. 1 shows the Morse potential representation of absorption and fluorescence transitions. $|\psi_v|^2$ is the square of the vibrational wavefunction for a given vibrational level.

While, at first glance, it might seem that fluorescence spectroscopy is simply another mode of observing electronic transitions, and is, therefore, little different from absorption measurements, there is a subtle fundamental difference between absorption and fluorescence measurements with respect to the band envelope that can potentially make the two modes of observation different, particulary with regard to the regression modeling of the band profile of the spectral data. This difference can be illustrated by the Morse-potential diagram shown in FIG. 1. As shown in FIG. 1, in absorption spectroscopy, an electronic transition occurs from the ground vibrational state of the ground electronic state to various excited vibrational levels of an excited electronic state. According to the Franck-Condon principle, an electronic transition will occur without changes in the positions of the nuclei (i.e., a vertical transition). In quantum mechanical terms, the probability of a transition is determined by $$|\langle \psi_e'' \psi_{v''} | M | \psi_e' \psi_{v'} \rangle|^2 \quad (1)$$

where $\psi_e$ is the electronic wavefunction, $\psi_v$ is the vibrational wavefunction (the double prime indicates the ground state and the single prime indicates the excited state), and M is the transition moment operator. In accord with the Born-Oppenheimer approximation, Eqn. 1 can be written as the product of two terms $$\langle \psi_e'' | M | \psi_e' \rangle^2 \langle \psi_{v''} | \psi_{v'} \rangle^2 \quad (2)$$

where the second term, known as the Franck-Condon factor, is the square of the overlap integral between the vibrational wavefunctions of the two states that are involved in the transition. Thus, in absorption, the strength of any given individual vibronic transition will be given by $$A \propto |\langle \psi_{v'} | \psi_{v''}=0 \rangle|^2 \quad (3)$$

and the band profile of the absorption band will be governed by the strengths of these individual vibronic transitions as determined by their respective Franck-Condon factors.

In fluorescence, the situation is somewhat different. Here a molecule is excited by absorption of a photon from the ground vibrational level of the ground electronic state to various excited vibrational levels of the excited electronic state (exactly as it was in absorption) as shown in FIG. 1. However, before the molecule has time to fluoresce, it undergoes vibrational relaxation to the lowest vibrational level of the excited electronic state. Fluorescence then occurs from the lowest vibrational level of the excited electronic state to various excited vibrational levels in the ground electronic state. So, in fluorescence, the intensity of any given vibronic transition will be given by $$I_{fluor} \propto |\langle \psi_{v'}=0 | \psi_{v''} \rangle|^2 \quad (4)$$

Once again, the band profile will be governed by the intensities of these individual vibronic transitions as determined by their respective Franck-Condon factors in Eqn. 4.

As shown in FIG. 1, a typical Morse potential for an anharmonic oscillator has a steep repulsive side (at short r, where r is the internuclear distance) and a less steep attractive side (at long r). In a $\pi \rightarrow \pi^*$ transition, it can be expected that the minimum of the upper state (which is $\pi^*$-like) will be shifted to longer r (less bound) as shown in FIG. 1, and absorption transitions will occur from v"=0 of the ground electronic state to the repulsive side of the upper state potential. As shown in FIG. 1, after vibrational relaxation, fluorescence transitions will occur to the attractive side of the ground-state potential well.

For situations like this, the Franck-Condon factors for absorption will be expected to be different from the Franck-Condon factors for fluorescence. Such differences should result in subtle differences in the shape of the band envelope that can be important in enantiomeric discrimination by regression analysis of spectral data. If the fluorescence process results in greater (or more uniform) spectral differences in the band envelope as a function of enantiomeric composition (i.e., greater enantiomeric discrimination), then fluorescence will be better than absorption when it comes to the regression modeling of the spectral data.

Naturally, in condensed-phase materials, the vibronic transitions that make up the band envelope will be broadened by solvent effects that arise from fluctuations in the structure of the solvation shell surrounding the chromophore. Such broadening is also likely to be affected by inclusion complex formation, which will affect both absorption and emission processes alike.

Multivariate modeling of the spectral data is a two-step procedure. In the first or calibration phase, a mathematical model in the form of a regression vector is determined with a training set of samples whose Y-variable is known. In particular, PLS-1 regression is used to construct a linear predictive model for enantiomeric compositions based on the spectral data. The equation below shows the typical format of a regression vector.

$$X_R = k_0 + k_1 A_1 + k_2 A_2 + \ldots + k_n A_n$$

In this equation, $X_R$ is the unknown mol fraction of guest molecule in the sample, $k_i$ are the coefficients of the regression vector, and $A_i$ are the absorbances at the different i wavelengths (i=1, ..., n) for a given unknown sample. The variable $k_0$ is a constant regression coefficient. The regression coefficients ($k_i$) and the regression constant ($k_0$) are calculated using the PLS-1 regression algorithm, which may preferably be performed on a computer system utilizing suitable software (Unscrambler®, CAMO, Oslo, Norway).

The PLS-1 algorithm is especially powerful as a means of regression because both the X- and the Y-data are actively involved in the construction of the new basis set made up of PLS components. In this way, the PLS regression algorithm focuses on those aspects of the data that are most important in predicting Y. Partial least-squares regression has a goal of minimizing sample response prediction error by seeking linear functions of the predictors that explain as much variation in each response as possible, as well as accounting for variation in the predictors. The techniques implemented in the PLS-1 procedure work by extracting successive linear combinations of the predictors. In particular, the PLS-1 method balances the two objectives, seeking factors that explain both response and predictor variation.

In the second or validation phase of multivariate modeling, the mathematical model developed for the training set of samples is used to predict the enantiomeric composition of another independently obtained set of samples whose enantiomeric composition is also known. Here, the spectral data for the validation set of samples are obtained, and the equation above is used to predict the enantiomeric composition of the samples in the set from the measured spectral data. In this phase, the values of the Y-data predicted by the model are compared with the known values for the validation set.

In particular, the methods for determining the enantiomeric composition of an unknown sample of a chiral compound involve the following steps. First, a series of samples is prepared using guest-host complexation, in which the guest molecule is the chiral compound whose enantiomeric composition is to be determined. The host molecule may vary, but is preferably cyclodextrin. The ratio of guest to host molecules remains the same, because the concentrations of guest and host molecules are at a fixed or preset level, and the enantiomeric compositions of the guest molecule are varied in each sample. Second, spectral data are collected for each sample at various wavelengths using spectroscopy. Third, principal component analysis is used to select a spectral range in which the spectral differences that arise in each sample due to the influence of the enantiomeric composition of the guest molecule are most appreciable. Fourth, PLS-1 regression of the spectral data for the selected wavelength range is performed for the data collected for each of the samples to determine the regression coefficients at each wavelength. Fifth, the calculated series of regression coefficient is entered into the regression vector.

Finally, a sample of the unknown compound is prepared through guest-host complexation, utilizing the same host compound, the same concentrations of guest and host compounds, and thus the same ratio of the chiral compound to the host compound. Spectral data for the sample is collected at each wavelength in the selected range of wavelengths and inserted into the regression vector, allowing the calculation of the enantiomeric composition.

The regression vector is represented by the following formula:

$$X_R = k_0 + k_1 A_1 + k_2 A_2 + \ldots + k_n A_n$$

wherein $X_R$ is the unknown enantiomeric composition of the chiral compound in the unknown sample, $k_i$ is the series of regression coefficients calculated for the selected range of wavelengths, $A_i$ is the spectral data of the unknown compound for the selected range of wavelengths, i is the selected range of wavelengths, 1–n, and $k_0$ is the constant regression coefficient. Thus, the regression coefficient at each wavelength is multiplied by the absorbance of the unknown sample measured at the same wavelength, to give a number represented as $k_i A_i$. This is done for each wavelength within the selected wavelength range. These numbers, along with the constant regression coefficient $k_0$, are then added together to give the enantiomeric composition of the unknown sample ($X_R$).

This strategy is useful for determining the enantiomeric compositions of various chiral compounds, including amino acids and pharmaceuticals. Any chiral compound that forms a complex with a host molecule and has an absorption band in the selected spectral range can be used. Examples of potential chiral guest compounds include chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds containing combinations of the above functionalities. In particular, the enantiomeric compositions of ibuprofen, norephedrine, phenylglycine ("φ-Gly"), tartaric acid, glycidyl butyrate, aspartic acid, phenylalanine, and arabinose can be determined. In the case of tartaric acid, the regression model has continued to correctly predict the enantiomeric composition of unknown samples for up to six months without the need for recalibration. Moreover, because the chiral analysis method does not depend on the specific rotation of the target molecule, it is especially valuable for compounds where polarimetric determinations are problematic due to small specific rotations.

Any homochiral compound known to be useful for complexation with chiral compounds may be used as a host compound in the guest/host complexation step. Preferably, the host compound possesses an inner hydrophobic cavity while being hydrophilic on the exterior. In preferred embodiments, cyclodextrin is used as the host molecule. Cyclodextrins are ideal inclusion complexing agents for solubilizing lipophilic guest molecules in aqueous media because they have a central cavity providing a hydrocarbon-like environment while the exterior of the cavity is water-compatible due to the oxygens linking the glucose units. In particular examples, the guest molecule may possess a phenyl group. The phenyl group will avoid the hostile hydrophilic environment of the aqueous solution in favor of the hydrophobic host molecule cavity, promoting the formation of the guest/host complex.

Both small and large guest molecules can form complexes with host molecules because complexation is not limited to the formation of 1:1 complexes where the guest is small enough to fit in the cavity. For large guest molecules, a number of host molecules may act cooperatively through multiple interactions to form n:1 (host:guest) complexes.

EXAMPLE 1

Generation of Regression Models for CD-Ibuprofen Complexes

Enantiomerically pure S-(+)-ibuprofen, as well as the racemic forms of ibuprofen, were obtained from Aldrich Chemical Co., Milwaukee, Wis. Homochiral α-cyclodextrin ("α-CD"), β-cyclodextrin ("β-CD"), and γ-cyclodextrin ("γ-CD") were also obtained from Aldrich. Stock solutions of cyclodextrins were prepared in deionized water. All solutions contained a fixed concentration of CD and a fixed concentration of ibuprofen. The CD-ibuprofen complexes were stabilized at pH 11 with a buffer prepared by mixing appropriate amounts of NaOH, $Na_2HPO_4$, and $KH_2PO_4$. Due to the non-availability of the pure enantiomeric form of R-(−)-ibuprofen, the regression model was constructed using samples with enantiomeric mole fractions in the range of 0.5–0.9. Spectra were recorded with a Hewlett-Packard photodiode array (Model 8455) UV-visible spectrophotometer over the wavelength range from 190–1100 nm. A quartz cell with a 1.0 cm path length was used. Multivariate regression was performed with a commercial chemometric software package (Unscrambler™ vers. 7.6, CAMO, Inc., Corvallis, Oreg.). Principal component analysis and partial least-squares regression were performed on the data using full cross-validation.

FIG. 1 shows the typical absorption spectra of 7.5 mM racemic ibuprofen, 7.5 mM S-(+)-ibuprofen, 7.5 mM a-cyclodextrin ("α-CD"), β-cyclodextrin ("β-CD"), and γ-cyclodextrin ("γ-CD"), as well as their respective complexes with ibuprofen at pH 11.1. The pH of the solution was maintained with phosphate buffer and sodium hydroxide. As shown in FIG. 1, solutions containing both ibuprofen and cyclodextrin show an increase in the absorbance of the guest molecule. Hyperchromic shifts of this type are indicative of CD guest-host complex formation. (Smith, et al., *J. Phys. Chem.*, vol. 98, pp. 8627–31, 1994; Dotsikas, et al., *J. Pharm. Biomed. Anal.*, vol. 23, pp. 997–1003, 2000).

Figure 2:
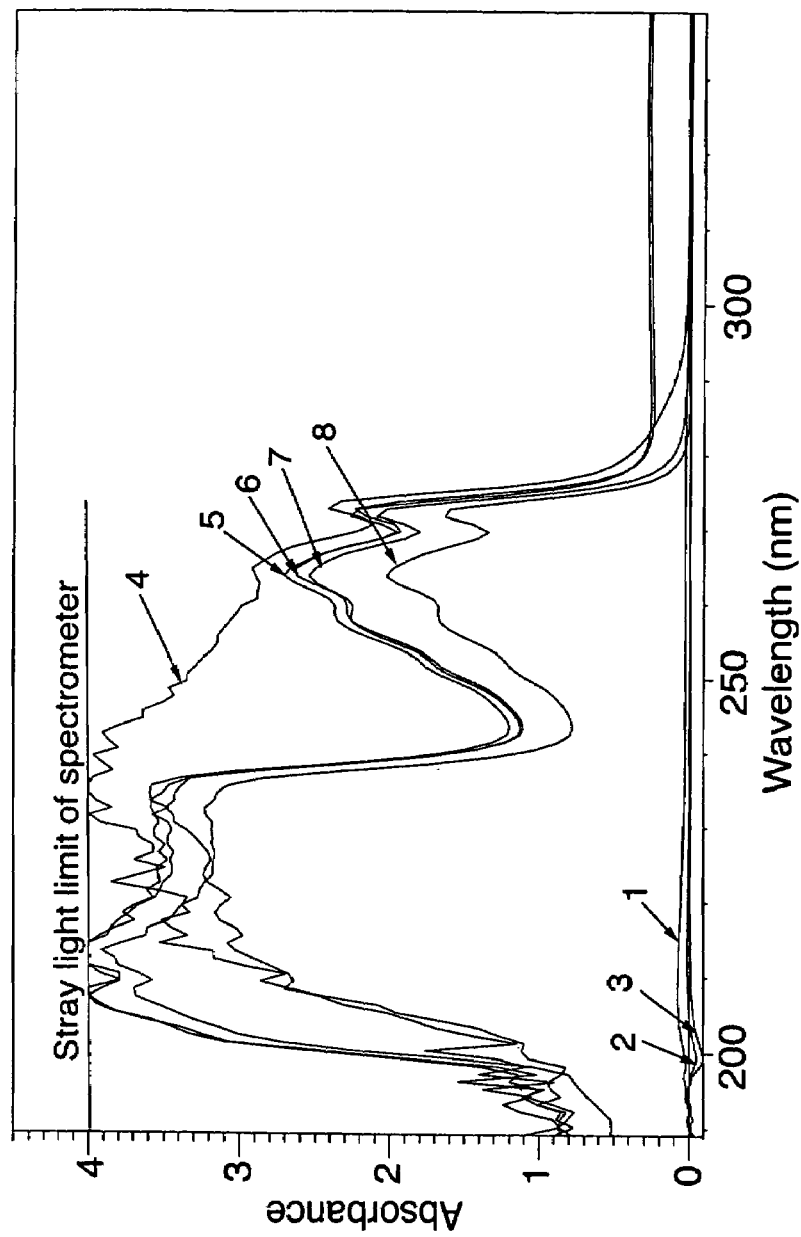
FIG. 2 shows the typical absorption spectra of (1) 7.5 mM β-cyclodextrin ("β-CD"), (2) 7.5 mM α-cyclodextrin ("α-CD"), (3) 7.5 mM γ-cyclodextrin ("γ-CD"), (4) 7.5 mM ibuprofen and 7.5 mM β-CD, (5) 7.5 mM ibuprofen and 7.5 mM α-CD, (6) 7.5 mM ibuprofen and 7.5 mM γ-CD, (7) 7.5 mM racemic ibuprofen, and (8) 7.5 mM S-(+)-ibuprofen, all at pH 11.1.

FIG. 2 shows the spectra obtained from 278–291 nm for a series of solutions. The spectral range was selected on the basis of principal component analysis. The solutions contain a fixed amount of β-CD (7.5 mM) and a fixed amount of S-ibuprofen (7.5 mM), where the enantiomeric composition of the ibuprofen was varied from mol fraction 0.55 to 0.95. As shown by the figure, the spectra clearly vary with enantiomeric composition. The region from 285 to 290 nm reveals three pseudo-isosbestic points, involving the crossing of two or more absorption spectra. The first occurs at 285 nm, where curves 8 and 9 cross. The second occurs at 288 nm, where curves 2 and 3 cross. The third occurs at 289 nm, where curves 4, 5, and 6 cross.

Figure 3:
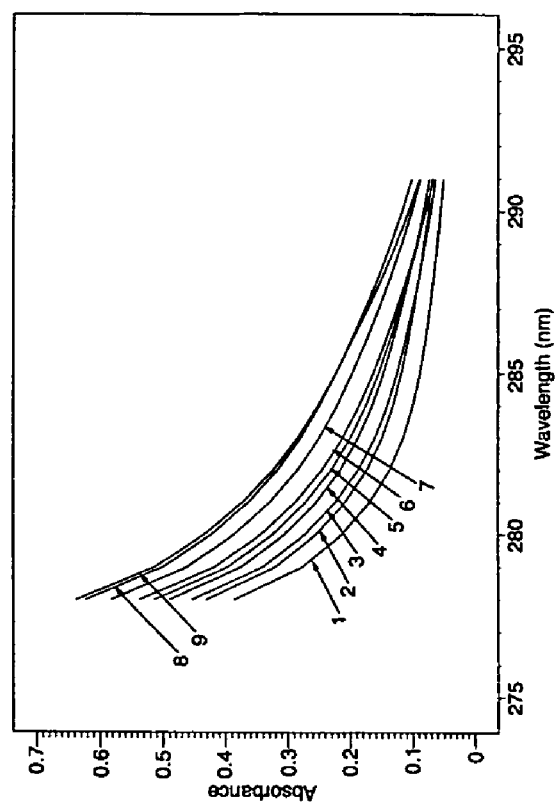
FIG. 3 shows the spectra obtained from 278–291 nm for a series of solutions containing a fixed amount of β-CD (7.5 mM) and a fixed amount of ibuprofen (7.5 mM), where the enantiomeric composition of the ibuprofen is a mole fraction of (1) 0.55, (2) 0.60, (3) 0.65, (4) 0.70, (5) 0.75, (6) 0.80, (7) 0.85, (8) 0.90, and (9) 0.95.

FIG. 3 shows the results for a PLS-1 regression of the spectral data over the wavelength range from 278–291 nm for guest-host complexes of ibuprofen and β-CD. In order to construct this model, nine ibuprofen solutions (all 7.5 mM) of different enantiomeric composition were prepared in 7.5 mM β-CD (pH 11.1) and the spectra were taken. FIG. 3*a* shows a scores plot of the first principal component ("PC1") versus the second principal component ("PC2"). This plot shows that all of the variation in the spectral data can be accounted for by PC1, along with 98% of the variation of the enantiomeric composition. The residual variance plot (FIG. 3c) shows that one principal component is all that is required to represent the data. Looking at the scores plot (FIG. 3a), the samples increase from sample 1 on the left (mol fraction S-ibuprofen 0.55) through sample 9 on the right (mol fraction S-ibuprofen 0.95) along PC1, indicating that PC1 is related to enantiomeric composition. FIG. 3b shows the regression coefficients obtained for the model as a function of wavelength. In this case, the regression coefficients are positive for wavelengths less than 285 nm, zero at 285 nm, and negative for wavelengths greater than 285 nm. FIG. 3d shows a plot of the concentration of S-ibuprofen predicted by the model versus the known values.

EXAMPLE 2

Influence of Host Molecule on Quality of CD-Ibuprofen Complex Regression Model

To investigate the influence of the host molecule on the quality of the regression model produced, studies were conducted with α-CD, β-CD, and γ-CD. Table 1 summarizes the results obtained with ibuprofen and the three cyclodextrins when the spectral data were correlated by means of PLS-1 regression with the known enantiomeric compositions of the ibuprofen used to prepare the guest-host complexes. A perfect model would have a correlation coefficient of 1, a slope of 1, and an offset of 0. As shown in Table 1, all three cyclodextrins produced good models with only slight variations in the model figures of merit.

TABLE 1

Summary of Figures of Merit for Regression Models Made for Ibuprofen

| System | Correlation Coefficient | Slope | Offset | Number of PCs used | Wavelength range (nm) |
|---|---|---|---|---|---|
| α-CD/Ibu[a] | 0.9987 | 0.9971 | $1.07 \times 10^{-5}$ | 5 | 279–295 |
| β-CD/Ibu[b] | 0.9999 | 0.9998 | $7.04 \times 10^{-7}$ | 5 | 279–292 |
| γ-CD/Ibu[c] | 0.9999 | 0.9998 | $6.15 \times 10^{-7}$ | 5 | 278–290 |

[a]7.5 mM α-CD and 7.5 mM ibuprofen, pH 11.1
[b]7.5 mM β-CD and 7.5 mM ibuprofen, pH 11.1
[c]7.5 mM γ-CD and 7.5 mM ibuprofen, pH 11.1

EXAMPLE 3

Use of CD-Ibuprofen Complex Regression Model to Predict Composition of Test Samples Table 2 gives the results obtained for a test set of 9 samples with varying mol fractions of S-(+)-ibuprofen for the three native CDs studied. The figure of merit used to compare the results is the root-mean-square error of prediction ("RMSEP"):

$$RMSEP = [\Sigma(Y_i - y_i)^2/n]^{0.5}$$

In this equation, $Y_i$ is the value predicted by the model for the $i^{th}$ sample, $y_i$ is the known value for the $i^{th}$ sample, and n is the number of samples in the test set. While all three CDs gave good results, those obtained with β-CD and γ-CD are somewhat better than those obtained with α-CD.

TABLE 2

Relative Errors Obtained for Ibuprofen with Independently Prepared Test Sets for the Three CDs Studied

| Actual mole fraction | α-CD Predicted mole fraction | Relative error (%) | β-CD Predicted mole fraction | Relative error (%) | γ-CD Predicted mole fraction | Relative error (%) |
|---|---|---|---|---|---|---|
| 0.580 | 0.556 | −4.14 | 0.580 | 0 | 0.579 | −0.17 |
| 0.636 | 0.632 | −0.63 | 0.634 | −0.31 | 0.635 | −0.16 |
| 0.690 | 0.678 | −1.74 | 0.694 | 0.58 | 0.688 | −0.29 |
| 0.715 | 0.706 | −1.26 | 0.712 | −0.42 | 0.716 | 0.14 |
| 0.780 | 0.777 | −0.38 | 0.773 | −0.90 | 0.786 | 0.77 |
| 0.840 | 0.891 | 6.07 | 0.834 | −0.71 | 0.835 | −0.59 |
| 0.867 | 0.893 | 3.00 | 0.878 | 1.27 | 0.881 | 1.61 |
| 0.915 | 0.915 | 0 | 0.906 | −0.98 | 0.915 | 0 |
| 0.940 | 0.947 | 0.74 | 0.931 | −0.96 | 0.945 | 0.53 |
| RMSEP (%) | | 2.76 | | 0.78 | | 0.66 |

EXAMPLE 4

Generation of Regression Models for CD-Norephedrine Complexes

Enantiomerically pure 1S,2R-(+)-norephedrine, 1R,2S-(−)-norephedrine, as well as α-cyclodextrin ("α-CD"), β-cyclodextrin ("β-CD"), and γ-cyclodextrin ("γ-CD") were obtained from Aldrich Chemical Co., Milwaukee, Wis. Stock solutions of cyclodextrins were prepared in deionized water. Stock solutions of the norephedrine enantiomers were prepared by dissolving the enantiomers in the stock cyclodextrin solution. All solutions contained a fixed concentration of CD and a fixed concentration of norephedrine. The enantiomeric composition of the calibration samples was varied from mol fraction 0.1 to 0.9. Spectra were recorded with a Hewlett-Packard photodiode array (Model 8455) UV-visible spectrophotometer over the wavelength range from 190–1100 nm. A quartz cell with a 1.0 cm path length was used. Multivariate regression was performed with a commercial chemometric software package (Unscrambler™ vers. 7.6, CAMO, Inc., Corvallis, Oreg.). Principal component analysis and partial least-squares regression were performed on the data using full cross-validation.

Figure 4:
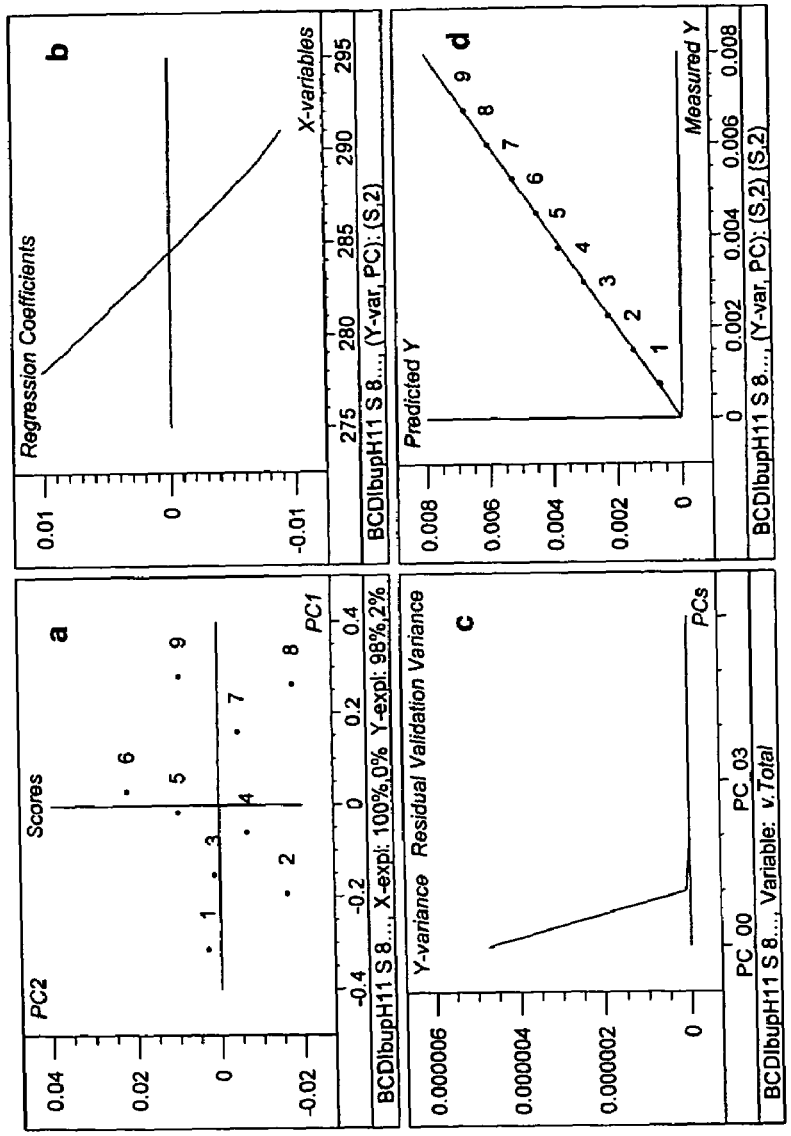
FIG. 4 shows a summary of the results for a PLS-1 regression of the spectral data over the wavelength range from 278–291 nm for guest-host complexes of ibuprofen and β-CD: (a) scores plot of the first principal component ("PC1") versus the second principal component ("PC2"); (b) regression coefficients as a function of wavelength; (c) residual variance as a function of the number of principal components; and (d) plot of the concentration of S-ibuprofen predicted by the model versus the known values.

FIG. 4 shows the typical absorption spectra of 7.5 mM 1S,2R-(+)-norephedrine, 7.5 mM 1R,2S-(−)-norephedrine, 15 mM α-CD, 15 mM β-CD, and 15 mM γ-CD, as well as mixtures containing 7.5 mM norephedrine and 15 mM cyclodextrin at neutral pH. As shown in FIG. 4, the addition of cyclodextrin to solutions containing a guest molecule (in this case, norephedrine) results in an increase in the absorbance of the guest molecule. This hyperchromic shift is taken as being indicative of CD guest-host complex formation, as it was in Example 1.

Figure 5:
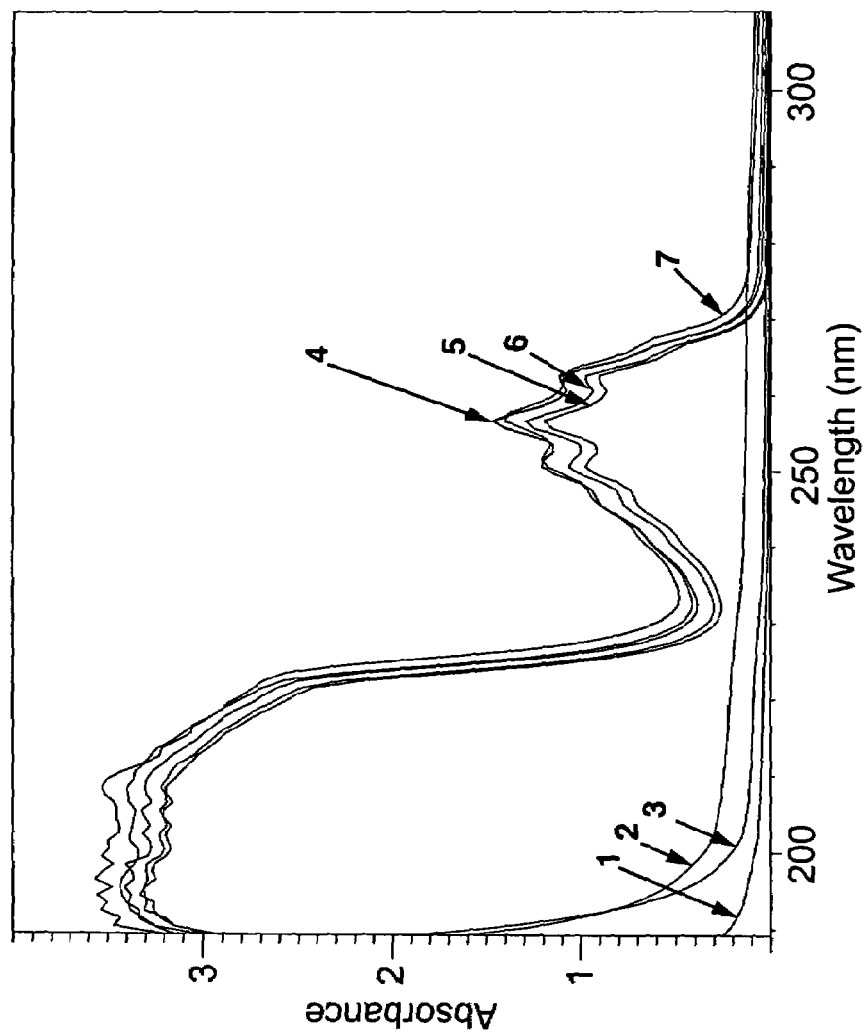
FIG. 5 shows the typical absorption spectra of (1) 15 mM α-CD, (2) 15 mM β-CD, (3) 15 mM γ-CD, (4) 15 mM α-CD and 7.5 mM norephedrine, and 15 mM γ-CD and 7.5 mM norephedrine, (5) 7.5 mM 1R,2S-(−)-norephedrine, (6) 7.5 mM 1S,2R-(+)-norephedrine, and (7) 7.5 mM norephedrine and 15 mM β-CD.

FIG. 5 shows the spectra obtained from 237–265 nm for a series of solutions. This particular wavelength range was selected on the basis of principal component analysis of the spectral data and represents the spectral region where the diastereomeric spectral differences that arise due to the influence of the enantiomeric composition are most appreciable. The solutions contain a fixed amount of γ-CD (15 mM) and a fixed amount of norephedrine (7.5 mM), where the enantiomeric composition of the 1S,2R-(+)-norephedrine was varied from mole fraction 0.1 to 0.9. As shown by the figure, the spectra vary with enantiomeric composition, although they appear too similar within the figure to label individually.

Figure 6:
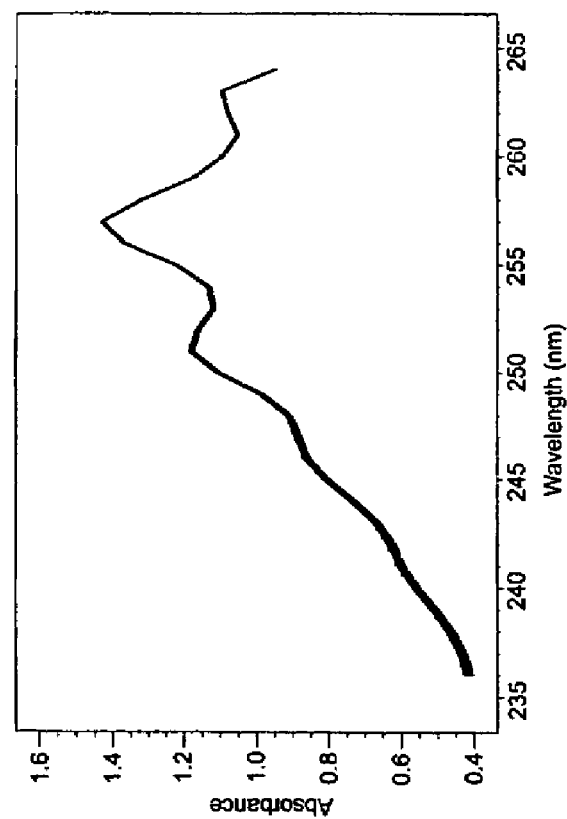
FIG. 6 shows the spectra obtained from 237–265 nm for a series of solutions containing a fixed amount of γ-CD (15 mM) and a fixed amount of norephedrine (7.5 mM), where the enantiomeric composition of the 1S,2R-(+)-norephedrine was varied from mole fraction 0.1 to 0.9. The spectra corresponding to specific mole fractions appear too similar to label individually on this scale.

FIG. 6 shows the results for a PLS-1 regression of the spectral data over the wavelength range from 237–265 nm for guest-host complexes of norephedrine and γ-CD. In order to construct this model, nine norephedrine solutions (all 7.5 mM) of different enantiomeric composition were prepared in 15 mM γ-CD and the spectra were taken. FIG. 6a shows a scores plot of the first principal component ("PC 1") versus the second principal component ("PC2"). This plot shows that 98% of the variation in the spectral data can be accounted for by PC1, along with 93% of the variation of the enantiomeric composition. FIG. 6b shows the regression coefficients obtained for the model as a function of wavelength. As shown in Example 1, the plot of the regression coefficients goes from positive to negative, but has additional variation as well.

EXAMPLE 5

Influence of Host Molecule on Quality of CD-Norephedrine Complex Regression Model To investigate the influence of the host molecule on the quality of the regression model produced, studies were conducted with α-CD, β-CD, and γ-CD. Table 3 summarizes the results obtained with norephedrine and the three cyclodextrins when the spectral data were correlated by means of PLS-1 regression with the known enantiomeric compositions of the norephedrine used to prepare the guest-host complexes. A perfect model would have a correlation coefficient of 1, a slope of 1, and an offset of 0. As shown in Table 3, all three cyclodextrins produced good models with only slight variations in the model figures of merit.

TABLE 3

Summary of Figures of Merit for Regression Models Made for Norephedrine

| System | Correlation Coefficient | Slope | Offset | Number of PCs used | Wavelength range (nm) |
|---|---|---|---|---|---|
| α-CD/Nor[a] | 0.9948 | 0.9898 | $3.73 \times 10^{-5}$ | 5 | 248–266 |
| β-CD/Nor[b] | 0.9996 | 0.9992 | $3.33 \times 10^{-6}$ | 5 | 246–262 |
| γ-CD/Nor[c] | 0.9990 | 0.9979 | $7.70 \times 10^{-6}$ | 5 | 237–265 |

[a]15 mM α-CD and 7.5 mM norephedrine
[b]15 mM β-CD and 7.5 mM norephedrine
[c]15 mM γ-CD and 7.5 mM norephedrine

EXAMPLE 6

Use of CD-Norephedrine Complex Regression Model to Predict Composition of Test Samples Table 4 gives the results obtained for a test set of 8 samples with varying mol fractions of 1S,2R-(+)-norephedrine for the three native CDs studied. The figure of merit used to compare the results is RMSEP, as it was in Example 3. Although the overall RMSEP for all three systems is less than 6%, once again the results obtained with β-CD and γ-CD are somewhat better than those obtained with α-CD.

TABLE 4

Relative Errors Obtained for Norephedrine with Independently Prepared Test Sets for the Three CDs Studied

| | α-CD | | β-CD | | γ-CD | |
|---|---|---|---|---|---|---|
| Actual mole fraction | Predicted mole fraction | Relative error (%) | Predicted mole fraction | Relative error (%) | Predicted mole fraction | Relative error (%) |
| 0.328 | 0.334 | 1.83 | 0.355 | 8.23 | 0.339 | 3.35 |
| 0.452 | 0.478 | 5.75 | 0.441 | −2.43 | 0.441 | −2.43 |
| 0.548 | 0.503 | −8.21 | 0.544 | −0.73 | 0.531 | −3.10 |
| 0.620 | 0.614 | −0.97 | 0.631 | 1.77 | 0.649 | 4.68 |
| 0.716 | 0.741 | 3.49 | 0.705 | −1.54 | 0.736 | 2.79 |
| 0.768 | 0.765 | −0.39 | 0.765 | −0.39 | 0.738 | −3.91 |
| 0.844 | 0.793 | −6.04 | 0.811 | −3.91 | 0.817 | −3.20 |
| 0.892 | 0.989 | 10.9 | 0.891 | −0.11 | 0.872 | 2.24 |
| RMSEP (%) | | 5.84 | | 3.45 | | 3.30 |

EXAMPLE 7

Generation of Regression Models for CD-Phenylglycine Complexes

Enantiomers of phenylglycine ("φ-Gly") were obtained commercially from Aldrich Chemical Co., Milwaukee, Wis. Spectra were recorded with a diode array UV visible spectrophotometer (Model 8453, Agilent Technologies, Palo Alto, Calif.) with a 1 nm sampling interval. A cell with a 1.0 cm path length was used. Multivariate regression was performed with a commercial chemometric software package (Unscrambler™ vers. 7.6, CAMO, Inc., Corvallis, Oreg.). Principal component analysis and partial least-squares regression were performed on the data using full cross-validation.

Figure 7:
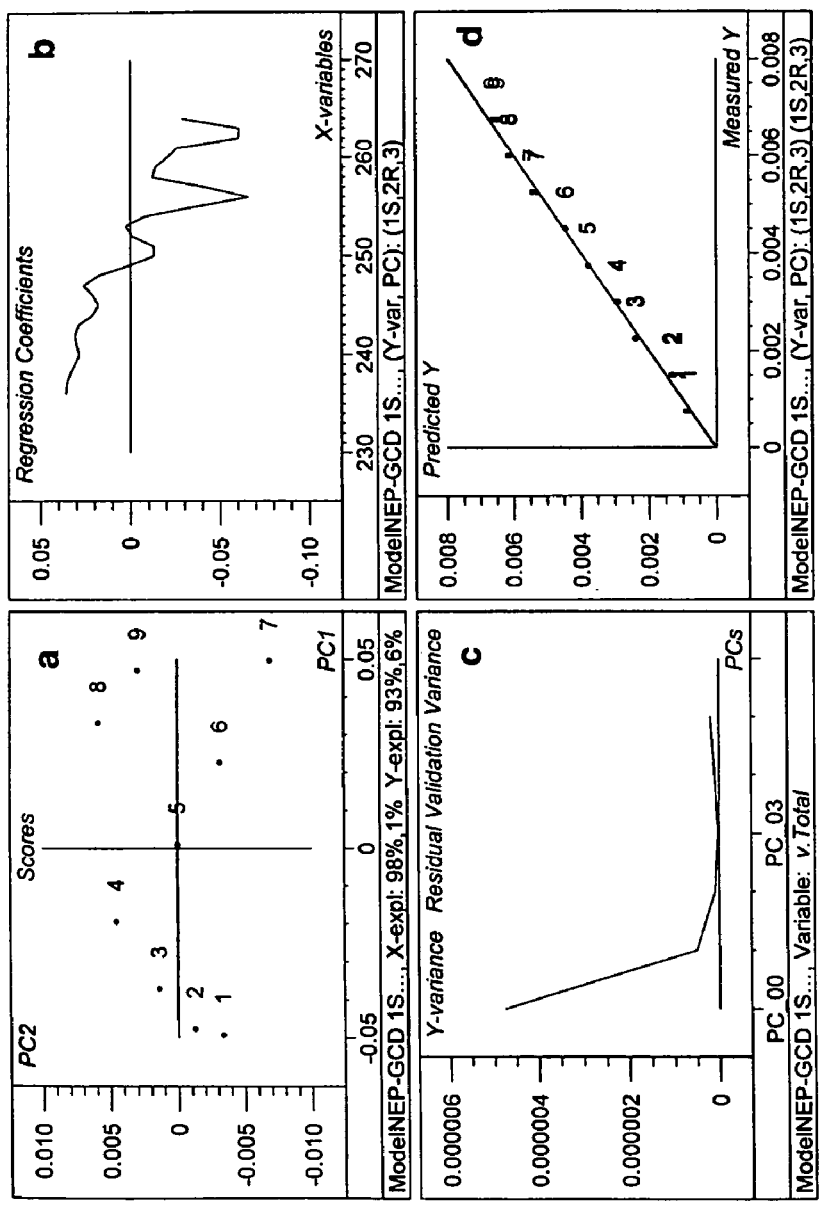
FIG. 7 shows a summary of the results for a PLS-1 regression of the spectral data over the wavelength range from 237–265 nm for guest-host complexes of norephedrine and γ-CD: (a) scores plot of the first principal component ("PC1") versus the second principal component ("PC2"); (b) regression coefficients as a function of wavelength; (c) residual variance as a function of the number of principal components; (d) plot of the concentration of 1S,2R-norephedrine predicted by the model versus the known values.

FIG. 7 shows the absorption spectra of 30 mM β-CD, 15 mM R-φ-Gly, 15 mM S-φ-Gly, and a mixture of 30 mM β-CD and 15 mM φ-Gly at pH 12. The spectra of pure R- and S-Gly are almost exactly coincident. When the CD and φ-Gly (either enantiomorph) are together in solution, the composite spectrum of the resulting mixture is not a sum of the intensities of the separate components, but resembles the spectrum of the uncomplexed φ-Gly shifted hyperchromically. This hyperchromic shift is taken as being indicative of CD guest-host complex formation, as it was in Example 1.

Figure 8:
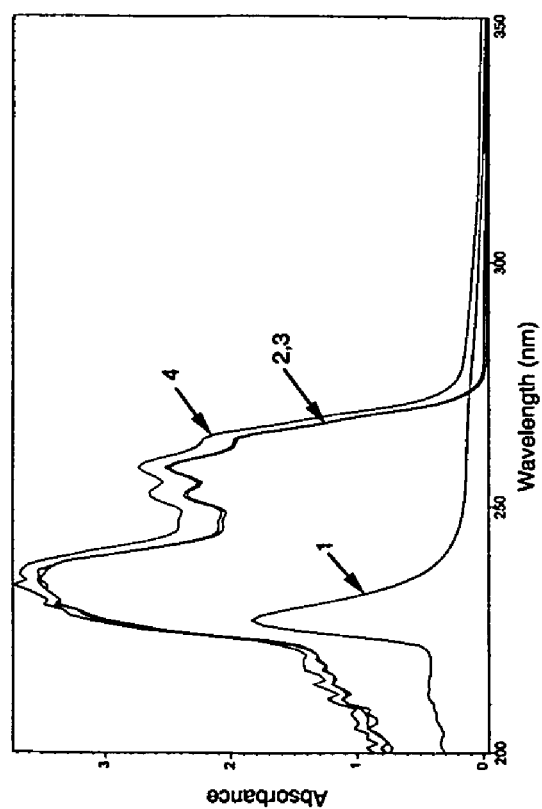
FIG. 8 shows the typical absorption spectra of (1) 30 mM β-CD, (2) 15 mM R-φ-Gly, (3) 15 mM S-φ-Gly, and (4) a mixture of 30 mM β-CD and 15 mM φ-Gly at pH 12.

FIG. 8 shows the absorption spectra obtained from 250–500 nm for a series of solutions. The solutions contained a fixed amount of β-CD (30 mM) and a fixed amount of R-φ-Gly (15 mM), where the enantiomeric composition of the R-φ-Gly was varied from mole fraction 0.5 to 0.9. As shown by the figure, the spectra vary with enantiomeric composition, although they appear too similar within the figure to label individually.

Figure 9:
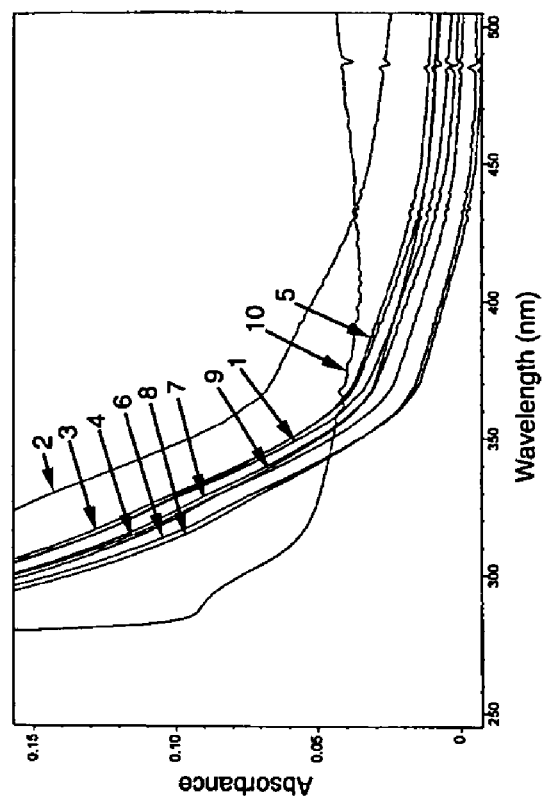
FIG. 9 shows the absorption spectra of solutions at pH 12 containing 30 mM β-CD and 15 mM φ-Gly of varying enantiomeric compositions: (1) 0.460, (2) 0.500, (3) 0.566, (4) 0.600, (5) 0.634, (6) 0.700, (7) 0.800, (8) 0.854, (9)0.900. Spectrum (10) is shown for 30 mM β-CD.
Figure 10:
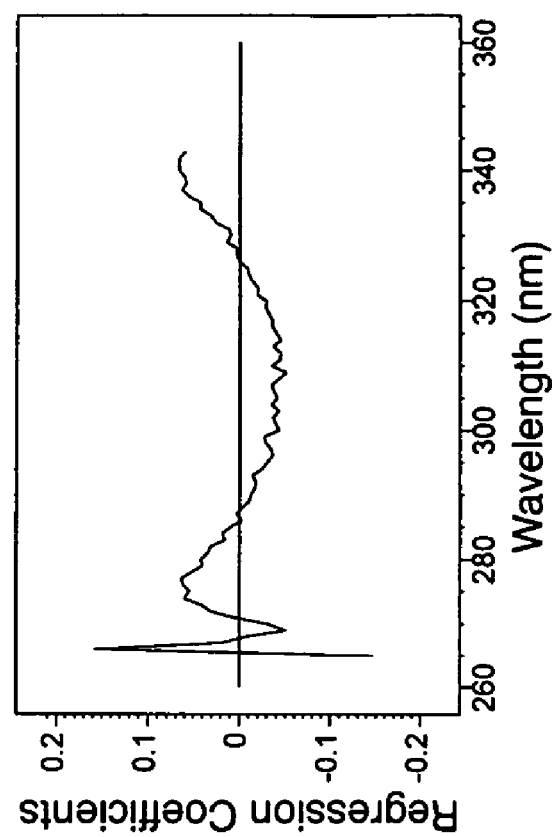
FIG. 10 shows the regression coefficients calculated by PLS-1 regression using R-φ-Gly as a function of wavelength from 260 to 345 nm at pH 12.

FIG. 9 shows the regression coefficients calculated by a PLS-1 regression using R-φ-Gly as a function of wavelength from 260 to 345 nm at pH 12. FIG. 10 shows a similar plot of the regression coefficients obtained for S-φ-Gly. Comparison of these two figures shows that they are reflections of one another about the xz plane. Thus, regression coefficients that are positive in the R-model are negative in the S-model.

EXAMPLE 8

Use of CD-Phenylglycine Complex Regression Model to Predict Composition of Test Samples Table 5 gives the results obtained for a test set of 6 samples with varying mol fractions of R-φ-Gly. The prediction results are in good agreement with the known values for the samples. A plot of the enantiomeric composition predicted by the model versus the known enantiomeric composition of the calibration set gave a straight line with a correlation coefficient of 0.955, a slope of 1.05, and an offset of $5.61 \times 10^{-4}$.

TABLE 5

Prediction Results Obtained with the Regression Model for R-φ-Gly

| Known mole fraction of R-φ-Gly | Predicted mole fraction of R-φ-Gly | Relative Error (%) |
|---|---|---|
| 0.528 | 0.515 | −2.46 |
| 0.620 | 0.581 | −6.29 |
| 0.673 | 0.673 | 0 |
| 0.727 | 0.753 | 3.58 |
| 0.827 | 0.873 | 5.56 |
| 0.873 | 0.873 | 0 |

EXAMPLE 9

Generation of Regression Models for CD-Aspartic Acid Complexes

Figure 11:
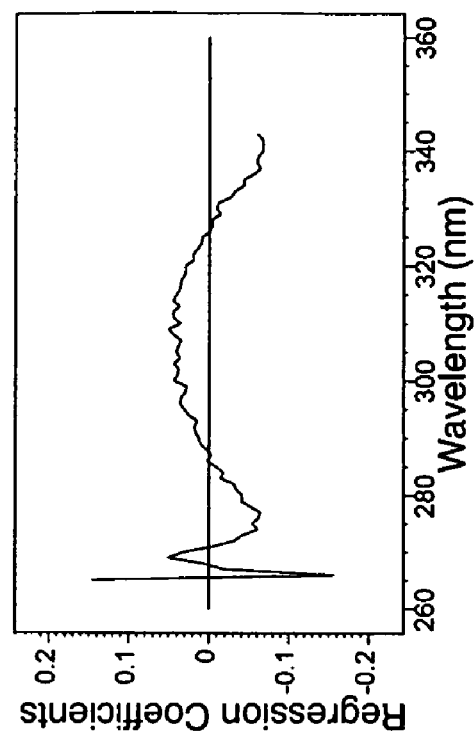
FIG. 11 shows the regression coefficients calculated by PLS-1 regression using S-φ-Gly as a function of wavelength from 260 to 345 nm at pH 12.

FIG. 11 shows the absorption spectra of 15 mM S-aspartic acid, 15 mM R-aspartic acid, 30 mM β-CD, and a mixture of 30 mM β-CD and 15 mM aspartic acid, all at pH 12.

Figure 12:
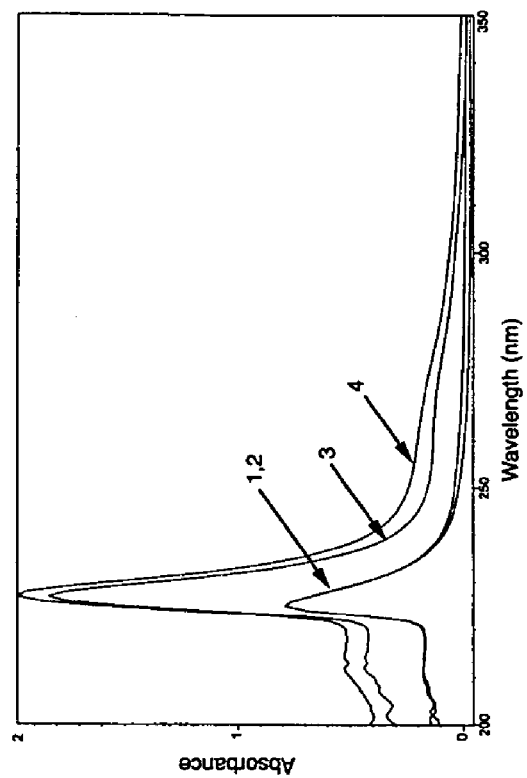
FIG. 12 shows the absorption spectra of (1) 15 mM S-aspartic acid, (2) 15 mM R-aspartic acid, (3) 30 mM β-CD, and (4) a mixture of 30 mM β-CD and 15 mM aspartic acid, all at pH 12.

FIG. 12 shows the spectra obtained from 250–380 nm for a series of solutions at pH 12. The spectral range was selected on the basis of principal component analysis. The solutions contain a fixed amount of β-CD (30 mM) and a fixed amount of aspartic acid (30 mM), where the enantiomeric composition of the guest molecule was varied from mol fraction 0.5 to 0.9. As shown by the figure, the spectra clearly vary with enantiomeric composition.

Figure 13:
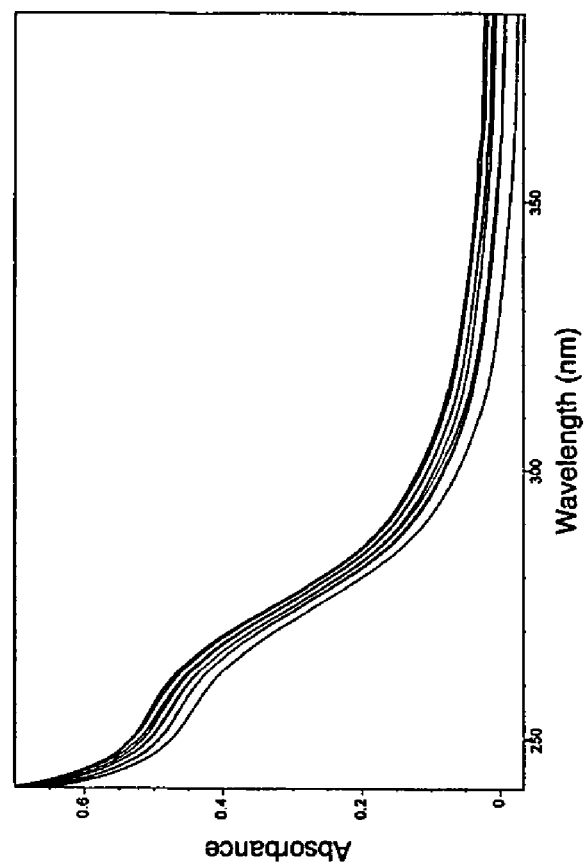
FIG. 13 shows the spectra obtained from 250–380 nm for a series of solutions at pH 12 containing a fixed amount of β-CD (30 mM) and a fixed amount of aspartic acid (30 mM), where the enantiomeric composition of the aspartic acid was varied from mol fraction 0.5 to 0.9. Spectra corresponding to specific mole fractions appear too similar to label individually on this scale.
Figure 14:
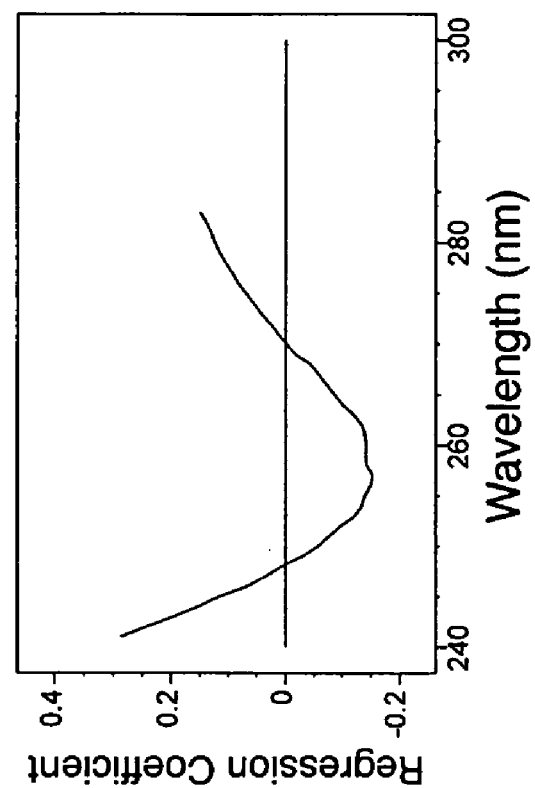
FIG. 14 shows the regression coefficients as a function of wavelength calculated by PLS-1 for the S-aspartic acid model from 240–285 nm at pH 12.

Using the spectral data collected and the known enantiomeric compositions of the solutions prepared from R- and S-aspartic acid standards, a PLS-1 regression model was developed. FIG. 13 shows the regression coefficients for the S-aspartic acid model and FIG. 14 shows the corresponding regression coefficients for the model developed for R-aspartic acid. The regression coefficients are shown as a function of wavelength from 240–285 nm at pH 12. As in Example 7, these figures are reflections of one another about the xz-plane.

Figure 15:
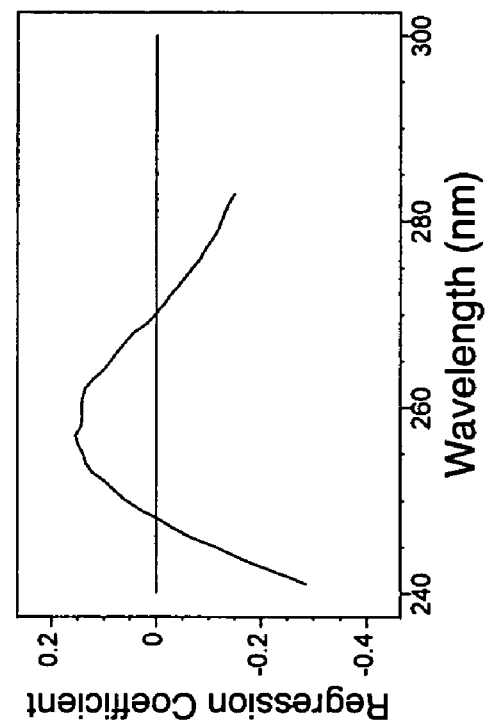
FIG. 15 shows the regression coefficients as a function of wavelength calculated by PLS-1 for the R-aspartic acid model from 240–285 nm at pH 12.
Figure 16:
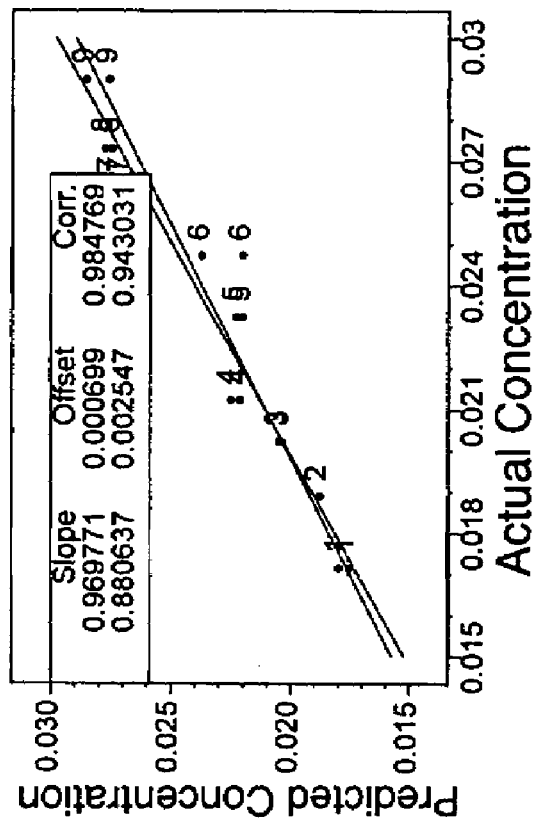
FIG. 16 shows a plot of the predicted concentration of R-aspartic acid versus the known concentration of the laboratory prepared standards (1–9). The line with the larger slope reflects the calibration model, while the line with the smaller slope reflects the validation model.

FIG. 15 shows a plot of the predicted concentration of R-aspartic acid versus the known concentration of the R-enantiomorph in laboratory prepared standards. Results from the calibration model (larger slope) and the model obtained using full cross validation are shown. Values for the slope, offset, and correlation coefficients are given for both models. A perfect model would have a slope of 1, an offset of zero, and a correlation coefficient of 1. As shown in the figure, the model provides a good fit for the data with no obvious outliers.

EXAMPLE 10

Use of CD-Aspartic Acid Complex Regression Model to Predict Composition of Test Samples Table 6 gives the results obtained for a test set of 7 samples with varying mol fractions of R-aspartic acid. All samples contained 30 mM β-CD and 30 mM aspartic acid, where the enantiomeric compositions of aspartic acid varied. The average magnitude of relative error is approximately 12%, about 4 times larger than that reported for φ-Gly. It is expected that the predictive ability of a given model ultimately depends on the magnitude of the diastereomeric interactions that occur in the complex, which, in turn, produce the spectral variations on which the model is based.

TABLE 6

Prediction Results Obtained with a Regression Model for R-Aspartic Acid

| Known mole fraction of R-aspartic acid | Predicted mole fraction of R-aspartic acid | Relative Error (%) |
|---|---|---|
| 0.660 | 0.680 | 3.03 |
| 0.700 | 0.693 | −1.00 |
| 0.760 | 0.597 | −21.4 |
| 0.800 | 0.613 | −23.4 |
| 0.860 | 0.813 | −5.47 |
| 0.900 | 0.773 | −14.1 |
| 0.960 | 0.820 | −14.6 |

EXAMPLE 11

Experimental Procedures for Determining Enantiomeric Purity Using Fluorescence Spectra Enantiomerically pure D-phenylalanine, L-phenylalanine, beta-cyclodextrin (β-CD), and gamma-cyclodextrin (γ-CD) were obtained from Aldrich Chemical Co. Stock solutions of cyclodextrins were prepared in deionized water. Stock solutions of the phenylalanine enantiomers were prepared by weighing the appropriate amounts of the two enantiomeric forms of phenylalanine and dissolving them in the stock cyclodextrin solution. For a given experiment, all solutions contained a fixed concentration of cyclodextrin and a fixed concentration of phenylalanine. The enantiomeric composition of the calibration samples was varied from mol fraction 0.100 to 0.900 of D-phenylalanine. The fluorescence spectra were recorded using a spectrofluorometer (FluoroMax-2, Jobin Yvon-SPEX Instruments, S.A.) A 1.0-cm path length fluorometer cell was used. Sample excitation was done at 257 nm and the emission was scanned between 250 and 500 nm. The excitation wavelength was selected based on the maximum absorption in the UV spectrum of phenylalanine. The spectra were dark off and blank corrected. The mean-centered spectral data were subjected to multivariate regression analysis using commercial chemometrics software (The Unscrambler™ vers. 7.6, CAMO, Inc., Corvalis, Oreg.). Partial least-squares regression (PLS-1) was performed on the calibration data using full cross-validation. The regression models developed were validated with independently prepared sets of validation samples.

EXAMPLE 12

Figure 17:
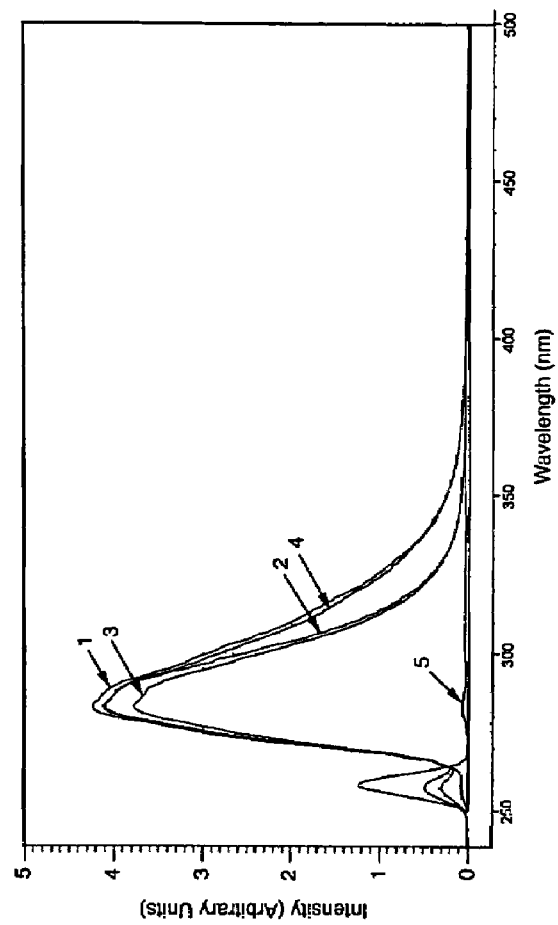
FIG. 17 shows the fluorescence emission versus wavelength for solutions of (1) 3.75 mM D-phenylalanine; (2) 3.75 mM L-phenylalanine; (3) 7.5 mM β-CD and 3.75 mM L-phenylalanine; (4) 7.5 mM β-CD and 3.75 mM D-phenylalanine; and (5) 7.5 mM β-CD.

Fluorescence Spectra of Phenylalanine, Cyclodextrin, and CD-Phenylalanine Complexes FIG. 17 shows the emission spectra obtained when samples of D-phenylalanine, L-phenylalanine, β-CD, and mixtures of phenylalanine and β-cyclodextrin were excited at 257 nm. The spectra are plotted as emission versus wavelength: 1. 3.75 mM D-phenylalanine; 2. 3.75 mM L-phenylalanine; 3. 7.5 mM β-CD and 3.75 mM L-phenylalanine; 4. 7.5 mM β-CD and 3.75 mM D-phenylalanine; and 5. 7.5 mM β-CD. Aside from a very small band in the vicinity of 280 nm, β-CD does not emit any significant fluorescence signal.

For samples containing phenylalanine, however, the $\pi \leftarrow \pi^*$ transition of the phenyl moiety at 282 nm is clearly evident. This singlet-to-singlet luminescence band arises from the symmetry forbidden $^1A_{1g} \rightarrow ^1B_{2u}$ absorption transition of the phenyl group. In water, the vibronic structure of this B-absorption band has a maximum at 258 nm. This forbidden secondary absorption band arises from the coupling of the electronic and vibrational wavefunctions of the phenyl group.

When β-CD is present in the solution along with phenylalanine, the intensity at the emission maximum (282 nm) is reduced for both enantiomeric forms of phenylalanine compared to that observed for the respective solutions containing only phenylalanine. Similar effects have been observed before in various spectral regions, and these spectral alterations have generally been taken to be indicative of inclusion complex formation (Smith, 1994 and Dotsikas, 2000).

FIG. 18a shows the fluorescence spectra from 200 nm to 500 nm obtained for nine samples of phenylalanine (3.75 mM) of different enantiomeric composition in the presence of β-CD. The nine samples had the following mole fractions of D-phenylalanine, respectively: 0.100; 0.200; 0.340; 0.400; 0.500; 0.600; 0.700; 0.800; and 0.900. All samples contained a fixed concentration (7.50 mM) of β-CD and were excited at 257 nm. The small band at 257 nm is due to scattered excitation radiation. In agreement with FIG. 17, the fluorescence emission spectrum consists of a single band at 282 nm due to the $\pi \leftarrow \pi^*$ transition of the phenyl ring. Although there is little difference in the spectra of the nine sample solutions on the short wavelength side of the emission band, notable spectral variations with enantiomeric composition of the phenylalanine are observed in the vicinity of the band maximum (280–292 nm) and along the long-wavelength side of the band (305–365 nm). FIG. 18b shows an expanded plot of the fluorescence spectra of the nine samples over the wavelength range from 310–375 nm. FIG. 18b gives a clearer indication of the how the envelope of the luminescence band varies with enantiomeric composition.

To get an even better indication of how the luminescence band of phenylalanine varies with enantiomeric composition of the chiral analyte in the presence of cyclodextrin, mean centering can be used. FIG. 19 shows the mean-centered spectral data from 261–444 nm for the nine samples after the mean spectrum has been subtracted from each spectrum. The nine samples contained 7.50 mM β-CD and 3.75 mM phenylalanine of the following mole fractions: 0.100; 0.200; 0.340; 0.400; 0.500; 0.600; 0.700; 0.800; and 0.900. This figure provides visual confirmation that the spectral variations observed in FIG. 18b are indeed the result of diastereomeric effects, presumably arising from inclusion complex formation.

While the spectral region in the vicinity of the emission band maximum (282 nm) clearly shows variation, the mean-centered spectra in this region do not appear to correlate particularly well with the enantiomeric composition of the samples and are not uniformly spaced along the ordinate. By contrast, the mean-centered spectra beyond 303 nm (on the long-wavelength side of the emission band) do readily correlate visually with enantiomeric composition with the maximum variation occurring at 318 nm. In addition, the spectra in the spectral region from about 309–393 nm are more or less uniformly displaced along the vertical axis. In this spectral region, the spectrum of the racemate (sample 5) is essentially at zero on the ordinate. Samples 1–4 with mol fractions of D-phenylalanine less than 0.5 have negative spectral signatures while samples 6–9 with mol fractions of D-phenylalanine greater than 0.5 have positive spectral signatures. Moreover, the curves with negative spectral signatures (1–4) appear, to a first approximation, to be related to the positive ones (6–9) by a $C_2$ rotation about the wavelength axis of the plot.

Thus, the spectral region that appears to correlate most closely with enantiomeric composition is the region from about 310–393 nm on the long-wavelength side of the emission band. Beyond 393 nm, all the spectra converge to essentially a single line. Since the $^1A_{1g} \rightarrow ^1B_{2u}$ absorption transition associated with the observed luminescence band involves the coupling of the electronic and vibrational wavefunctions of the molecule, it is perhaps not surprising that inclusion complex formation with homochiral cyclodextrins results in diastereomeric effects that alter the band envelope of the emission band.

Figure 20:
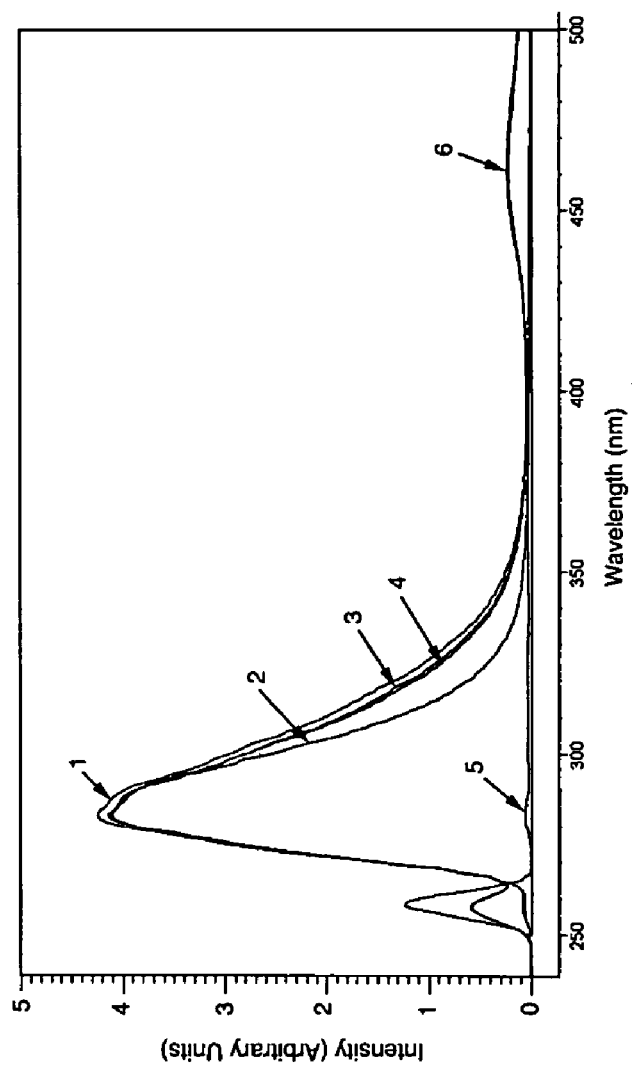
FIG. 20 shows the fluorescence emission versus wavelength for solutions of: (1) 3.75 mM D-phenylalanine; (2) 3.75 mM L-phenylalanine; (3) 7.5 mM γ-CD and 3.75 mM D-phenylalanine; (4) 7.5 mM γ-CD and 3.75 mM L-phenylalanine; (5) 7.5 mM γ-CD; (6) 7.5 mM γ-CD and 3.75 mM D-phenylalanine; and (7) 7.5 mM γ-CD and 3.75 mM L-phenylalanine.

FIG. 20 shows the emission spectra obtained when samples of D-phenylalanine, L-phenylalanine, γ-CD, and mixtures of phenylalanine and γ-cyclodextrin were excited at 257 nm. The seven samples tested contained: (1) 3.75 mM D-phenylalanine; (2) 3.75 mM L-phenylalanine; (3) 7.5 mM γ-CD and 3.75 mM D-phenylalanine; (4) 7.5 mM γ-CD and 3.75 mM L-phenylalanine; (5) 7.5 mM γ-CD; (6) 7.5 mM γ-CD and 3.75 mM D-phenylalanine; and (7) 7.5 mM γ-CD and 3.75 mM L-phenylalanine. From the figure, it is apparent that γ-CD does not emit any significant fluorescence signal. Once again, for samples containing phenylalanine, the $\pi \leftarrow \pi^*$ transition of the phenyl moiety at 282 nm is clearly evident. While the spectra for solutions containing phenylalanine and γ-CD are similar to those shown in FIG. 17 for phenylalanine and β-CD, FIG. 20 reveals the presence of a weak band at 460 nm that was not present with solutions containing phenylalanine and β-CD. Since this band is only present in solutions containing both phenylalanine and γ-CD, it is not due to impurities in the reagents and must, therefore, be due to inclusion complex formation. While the exact origin of the band is uncertain at this time, it is interesting to note that the appearance of exciplex emission in roughly the same wavelength region (~500 nm) is reported for inclusion complexes involving γ-CD (Jiang and Xu, 2001). If this band is the result of exciplex emission, its presence provides additional evidence for inclusion complex formation.

FIG. 21a shows the fluorescence spectra from 200 to 500 nm for nine samples of phenylalanine (3.75 mM) of different enantiomeric compositions in the presence of 7.50 mM γ-CD. The mole fractions of D-phenylalanine were: 0.100; 0.200; 0.340; 0.400; 0.500; 0.600; 0.700; 0.800; and 0.900, respectively. Once again, the samples were excited at 257 nm. Once again, definite spectral variations are observed with phenylalanine samples of different enantiomeric compositions. The enantiomeric discrimination regions shown in FIG. 21a are similar to those observed in FIG. 18a with the exception of the new small band in the 420–500 nm region that also shows some spectral variation. FIG. 21b shows an expanded plot of the fluorescence spectra of the nine samples in the presence of γ-CD over the wavelength range from 320–375 nm. By contrast with FIG. 18b, the spacing of the spectra in FIG. 21b is more uniform.

Figure 22:
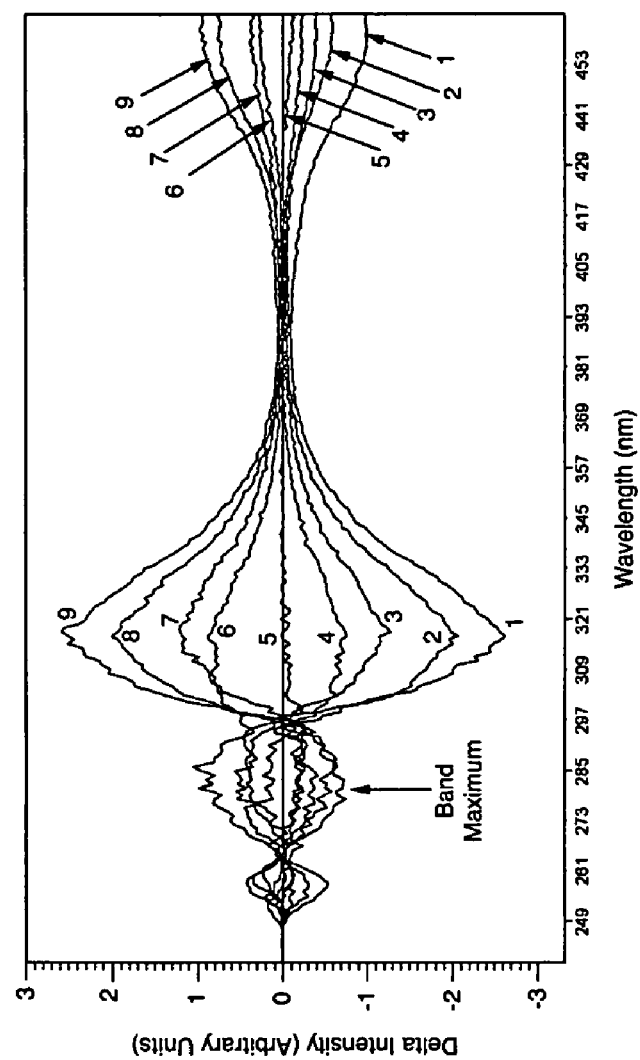
FIG. 22 the mean-centered fluorescence emission spectra from 249–465 nm of nine samples containing 7.50 mM γ-CD and 3.75 mM phenylalanine of various enantiomeric compositions.

FIG. 22 shows the mean-centered spectral data from 261–465 nm for the nine samples after the mean spectrum has been subtracted from each spectrum. The nine samples contained phenylalanine (3.75 mM) of different enantiomeric compositions in the presence of 7.50 mM γ-CD. The mole fractions of D-phenylalanine were: 0.100; 0.200; 0.340; 0.400; 0.500; 0.600; 0.700; 0.800; and 0.900, respectively. Once again, the mean-centered spectra beyond 303 nm do appear to correlate visually with enantiomeric composition with the maximum variation occurring at 318 nm. In addition, the spectra in the spectral region from about 309–393 nm are more or less uniformly displaced along the vertical axis. In this spectral region, the spectrum of the racemate (sample 5) is essentially at zero on the ordinate. Samples 1–4 with mol fractions of D-phenylalanine less than 0.5 have negative spectral signatures while samples 6–9 with mol fractions of D-phenylalanine greater than 0.5 have positive spectral signatures. Once again, the curves with negative spectral signatures (1–4) appear, to a first approximation, to be related to the positive ones (6–9) by a $C_2$ rotation about the wavelength axis of the plot.

As shown in FIG. 22, the new band observed at 460 nm also shows significant variation with enantiomeric composition. It is interesting to note that with this band the spectral variation at the band maximum does appear to correlate with enantiomeric composition.

Figure 18:
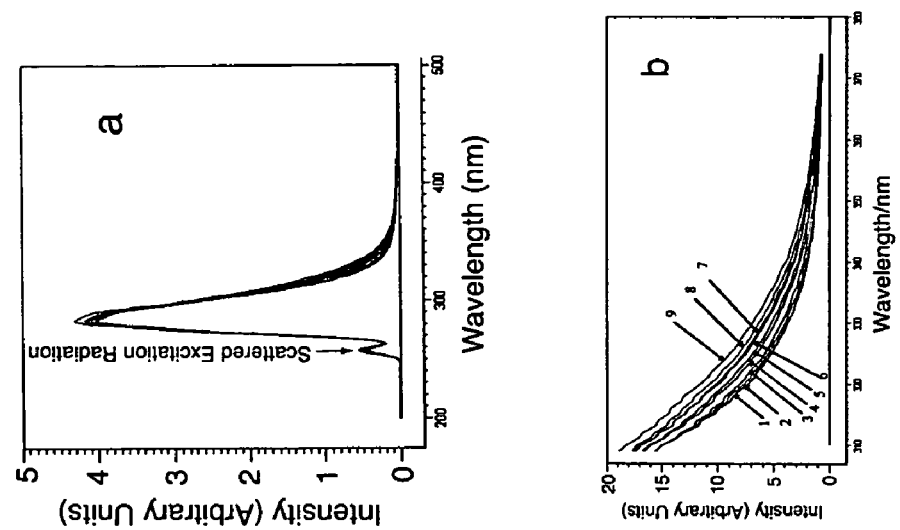
FIG. 18 shows the fluorescence emission spectra of nine samples of phenylalanine, with excitation at 257 nm: (a) fluorescence emission spectra from 200–500 nm of nine samples containing 7.50 mM β-CD and 3.75 mM phenylalanine of various enantiomeric compositions; (b) expanded view of fluorescence emission spectra from 310–370 nm of nine solutions containing 7.50 mM β-CD and 3.75 mM phenylalanine of various enantiomeric compositions.
Figure 19:
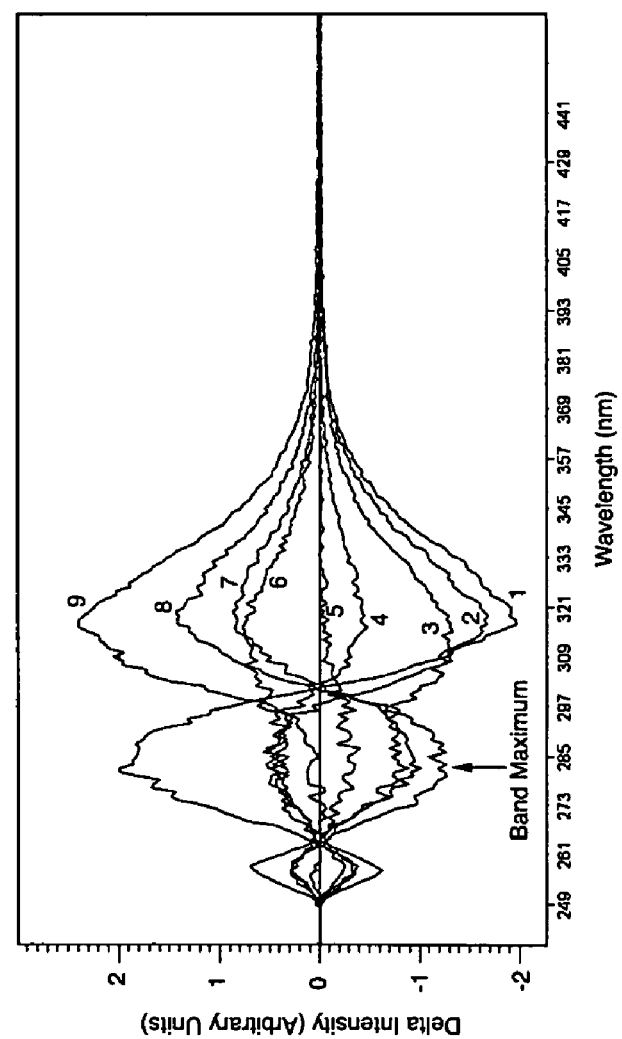
FIG. 19 shows the mean-centered fluorescence emission spectra from 249–444 nm of nine samples containing 7.50 mM β-CD and 3.75 mM phenylalanine of various enantiomeric compositions.
Figure 21:
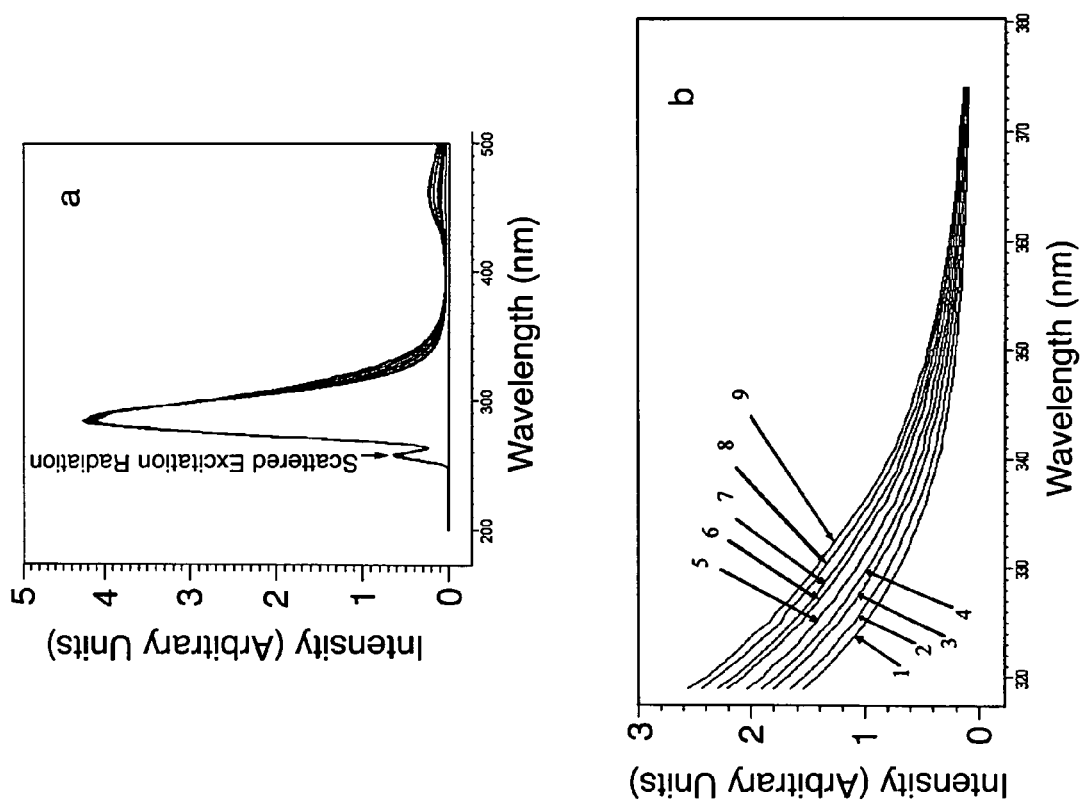
FIG. 21 shows the fluorescence emission spectra of nine samples of phenylalanine, with excitation at 257 nm: (a) fluorescence emission spectra from 200–500 nm of nine samples containing 7.50 mM γ-CD and 3.75 mM phenylalanine of various enantiomeric compositions; (b) expanded view of fluorescence emission spectra from 310–370 nm of nine solutions containing 7.50 mM γ-CD and 3.75 mM phenylalanine of various enantiomeric compositions.

FIGS. 18 and 21 show that definite spectral changes do indeed occur as the enantiomeric composition of the phenylalanine is varied (while keeping the total concentrations of phenylalanine and cyclodextrin fixed). The observed spectral changes are small, however, and occur in solutions containing mixtures of complexed and uncomplexed guest and host molecules. In circumstances such as these, multivariate regression modeling is frequently useful because it can focus on those spectral features that correlate with the parameter of interest (in this case, enantiomeric composition), while ignoring those spectral features that do not correlate.

EXAMPLE 13

Generation and Relative Errors of Regression Models for CD-Phenylalanine Complexes To determine the usefulness of PLS-1 regression modeling of fluorescence spectral data of the type illustrated in FIGS. 17b and 20b, a series of regression models was developed with a widely used commercial multivariate analysis software package. Each training set used to develop the particular regression model consisted of nine samples whose enantiomeric composition was known from the masses of the enantiomers used to prepare the samples. The raw spectral data (see FIGS. 17a and 20a) were automatically mean-centered by the software package prior to regression modeling. The regression models obtained were then subsequently validated by using them to predict the enantiomeric composition of independently prepared sets of validation samples from the fluorescence spectral data of the samples.

Four studies were conducted using different fixed concentrations of phenylalanine and cyclodextrin. In each study, the concentration of cyclodextrin was twice that of the phenylalanine to insure that there was an excess of host molecule available for complexation. Table 7 below gives the concentrations, the wavelength ranges, and the number of PLS components used to make the regression models.

TABLE 7

Parameters for the four regression models

| Model | Cyclodextrin concentration (mM) | Phenylalanine concentration (mM) | Wavelength range (nm) | PLS Components |
|---|---|---|---|---|
| 1 | 7.50 | 3.75 | 310–375 | 5 |
| 2 | 3.75 | 1.88 | 310–360 | 5 |
| 3 | 1.88 | 0.938 | 320–375 | 5 |
| 4 | 0.938 | 0.469 | 315–375 | 5 |

Tables 8–11 below give the prediction results obtained for both enantiomers of phenylalanine when each model was validated with an independently prepared set of nine validation samples. Each validation sample was prepared gravimetrically in the same manner as used to prepare the calibration samples used initially to develop the regression model. Although the concentrations of the validation samples were the same as those used to prepare the regression model initially, the enantiomeric compositions of the samples were different from those used to develop the model. The root-mean-square percent relative error (RMS % RE), given by $$RMS\ \%\ RE = \sqrt{\frac{\Sigma (\%\ RE_i)^2}{n}} \qquad (5)$$

—where % $RE_i$ is the percent relative error calculated from the known and predicted values for the $i^{th}$ validation sample, and n is the number of validation samples in the set—was used as a figure of merit to evaluate the predictive ability of the models.

TABLE 8

Relative Errors for Regression Model 1

| | | β-CD | | | | γ-CD | | | |
|---|---|---|---|---|---|---|---|---|---|
| Actual mol fraction D | Actual mol fraction L | Predicted mol fraction D | % relative error for D | Predicted mol fraction L | % relative error for L | Predicted mol fraction D | % relative error for D | Predicted mol fraction L | % relative error for L |
| 0.264 | 0.736 | 0.254 | −3.8 | 0.746 | 1.4 | 0.269 | 2 | 0.731 | −0.7 |
| 0.328 | 0.672 | 0.341 | 4.0 | 0.659 | −1.9 | 0.328 | 0 | 0.672 | 0 |
| 0.452 | 0.548 | 0.464 | 2.7 | 0.536 | −2.2 | 0.445 | −2 | 0.555 | 1 |
| 0.548 | 0.452 | 0.564 | 2.9 | 0.436 | −3.5 | 0.552 | 0.7 | 0.448 | −0.9 |
| 0.620 | 0.380 | 0.616 | −0.6 | 0.384 | 1 | 0.600 | −3.2 | 0.400 | 5.3 |
| 0.715 | 0.285 | 0.725 | 1.4 | 0.275 | −3.5 | 0.731 | 2.2 | 0.269 | −5.6 |
| 0.752 | 0.248 | 0.769 | 2.3 | 0.231 | −6.9 | 0.787 | 4.6 | 0.213 | −14 |
| 0.844 | 0.156 | 0.848 | 0.5 | 0.152 | −3 | 0.825 | −2.2 | 0.175 | 12 |
| 0.892 | 0.108 | 0.874 | −2.0 | 0.126 | 17 | 0.880 | −1.3 | 0.120 | 11 |
| RMS % RE | | | 2.5 | | 6.5 | | 2.4 | | 7.6 |

TABLE 9

Relative Errors for Regression Model 2

| | | β-CD | | | | γ-CD | | | |
|---|---|---|---|---|---|---|---|---|---|
| Actual mol fraction D | Actual mol fraction L | Predicted mol fraction D | % relative error for D | Predicted mol fraction L | % relative error for L | Predicted mol fraction D | % relative error for D | Predicted mol fraction L | % relative error for L |
| 0.264 | 0.736 | 0.264 | 0 | 0.736 | 0 | 0.263 | −0.4 | 0.737 | 0.1 |
| 0.328 | 0.672 | — | — | | | 0.338 | 3.0 | 0.662 | −1.5 |
| 0.452 | 0.548 | 0.439 | −2.9 | 0.561 | 2.4 | 0.451 | −0.2 | 0.549 | 0.2 |
| 0.548 | 0.452 | 0.565 | 3.1 | 0.435 | −3.8 | 0.554 | 1 | 0.446 | −1 |
| 0.620 | 0.380 | 0.580 | −6.4 | 0.420 | 11 | 0.612 | −1 | 0.388 | 2 |
| 0.715 | 0.285 | 0.712 | −0.4 | 0.288 | 1 | 0.702 | −1.8 | 0.298 | 4.6 |
| 0.752 | 0.248 | 0.775 | 3.1 | 0.225 | −9.3 | 0.730 | −2.9 | 0.270 | 8.9 |
| 0.844 | 0.156 | 0.844 | 0 | 0.156 | 0 | 0.853 | 1.1 | 0.147 | −6 |
| 0.892 | 0.108 | 0.877 | −1.7 | 0.123 | 14 | 0.873 | −2.1 | 0.127 | 18 |
| RMS % RE | | | 3.0 | | 7.3 | | 1.8 | | 7.2 |

TABLE 10

Relative Errors for Regression Model 3

| | | β-CD | | | | γ-CD | | | |
|---|---|---|---|---|---|---|---|---|---|
| Actual mol fraction D | Actual mol fraction L | Predicted mol fraction D | % relative error for D | Predicted mol fraction L | % relative error for L | Predicted mol fraction D | % relative error for D | Predicted mol fraction L | % relative error for L |
| 0.264 | 0.736 | 0.260 | −2 | 0.740 | 0.5 | 0.280 | 6.1 | 0.720 | −2.2 |
| 0.328 | 0.672 | 0.333 | 2 | 0.667 | −0.7 | 0.322 | −2 | 0.678 | 0.9 |
| 0.452 | 0.548 | 0.428 | −5.3 | 0.572 | 4.4 | 0.445 | −2 | 0.555 | 1 |
| 0.548 | 0.452 | 0.542 | −1 | 0.458 | 1.3 | 0.522 | −4.7 | 0.478 | 5.8 |
| 0.620 | 0.380 | 0.594 | −4.2 | 0.406 | 6.8 | 0.591 | −4.7 | 0.409 | 7.6 |
| 0.715 | 0.285 | 0.703 | −1.7 | 0.297 | 4.2 | 0.675 | −5.6 | 0.325 | 14 |
| 0.752 | 0.248 | 0.758 | 0.8 | 0.242 | −2.4 | 0.748 | −0.5 | 0.252 | 2 |
| 0.844 | 0.156 | 0.830 | −1.7 | 0.170 | 9.0 | 0.813 | −3.7 | 0.187 | 20 |
| 0.892 | 0.108 | 0.888 | −0.4 | 0.112 | 4 | 0.868 | −2.7 | 0.132 | 22 |
| RMS % RE | | | 2.5 | | 4.6 | | 4.0 | | 11 |

TABLE 11

Relative Errors for Regression Model 4

| | | β-CD | | | | γ-CD | | |
|---|---|---|---|---|---|---|---|---|
| Actual mol fraction D | Actual mol fraction L | Predicted mol fraction D | % relative error for D | Predicted mol fraction L | % relative error for L | Predicted mol fraction D | % relative error for D | Predicted mol fraction L | % relative error for L |
| 0.264 | 0.736 | 0.266 | 0.8 | 0.734 | −0.3 | 0.278 | 5.3 | 0.722 | −1.9 |
| 0.328 | 0.672 | 0.333 | 2 | 0.667 | −0.7 | 0.325 | −0.9 | 0.675 | 0.4 |
| 0.452 | 0.548 | 0.443 | −2 | 0.557 | 2 | 0.441 | −2.4 | 0.559 | 2.0 |
| 0.548 | 0.452 | 0.546 | −0.4 | 0.454 | 0.4 | 0.555 | 1 | 0.445 | −2 |
| 0.620 | 0.380 | 0.624 | 0.6 | 0.376 | −1 | 0.603 | −2.7 | 0.397 | 4.5 |
| 0.715 | 0.285 | 0.730 | 2.1 | 0.270 | −5.3 | 0.700 | −2.1 | 0.300 | 5.3 |
| 0.752 | 0.248 | 0.762 | 1.3 | 0.238 | −4.0 | 0.770 | 2.4 | 0.230 | −7.3 |
| 0.844 | 0.156 | 0.842 | −0.2 | 0.158 | 1 | 0.858 | 1.7 | 0.142 | −9.0 |
| 0.892 | 0.108 | 0.894 | 0.2 | 0.106 | −2 | 0.900 | 0.9 | 0.100 | −7 |
| RMS % RE | | | 1.3 | | 2.5 | | 2.5 | | 5.2 |

To test the stability of the regression model for the prediction of the enantiomeric composition of future phenylalanine samples, the validation study involving 0.938 mM cyclodextrin and 0.469 mM phenylalanine was repeated on two more occasions under the same experimental conditions approximately one week after the original model was developed. For these experiments, new spectral data were collected on two new sets of validation samples and the enantiomeric composition of the new validation samples was predicted with the original regression model developed earlier. The results obtained from the repeat experiments were reproducible and comparable with results of the initial study. The average RMS % RE in the mol fraction of D-phenylalanine from the two repeat experiments where β-CD was the host was 5.0%, while the two repeat experiments with γ-CD gave an average RMS % RE in the mol fraction of D-phenylalanine of 4.5%.

It is interesting to note that the RMS % RE in the determination of the mol fraction of L-phenylalanine given in Tables 8–11 is roughly two to three times larger than that observed with D-phenylalanine. Close examination of the results shown in these tables reveals that most of this increased error in the determination of L-phenylalanine is associated with samples where the mol fraction of D-phenylalanine is greater than 0.8. This is a natural consequence of the fact that the predicted mol fraction of L-phenylalanine was calculated by difference using the predicted mol fraction for D-phenylalanine (i.e., the mol fraction of L-phenylalanine was determined indirectly). Thus, while the predicted values of the mol fraction of D-phenylalanine for samples where the mol fraction of D-phenylalanine is greater than 0.8 are generally quite good, any small errors in the determination of D-phenylalanine will produce correspondingly larger errors in the predicted results for L-phenylalanine because the mol fraction of L-phenylalanine is relatively small. In addition, a positive error in the predicted mol fraction of D-phenylalanine will produce a corresponding negative error in the predicted mol fraction of L-phenylalanine and vice versa. Therefore, if information on both enantiomers is required, it is actually better to model each one independently rather than calculating one isomer from a model made for the other.

REFERENCES CITED

Other Publications

Balabai, J. Phys. Chem., vol. 102, p. 9617, 1998
Bortolus, et al., J. Phys. Chem. A, vol. 106, p. 1686, 2002
Cox, et al., J. Photochem. Photobiol., vol. 39, p. 597, 1984
Dotsikas, et al., J. Pharm. Biomed. Anal., vol. 23, pp. 997–1003, 2000
Jiang, H. and H. Xu, J. Chem Soc. Perkin Trans., vol. 2, pp. 1274–79, 2001
Otagiri, et al., Chem. Pharm. Bull., vol. 23, p. 188, 1975
Park, et al., J. Phys. Chem., vol. 98, p. 6158, 1994
Schiller, et al., J. Chem. Soc., Faraday Trans., vol. 83, p. 3227, 1987
Smith, et al., J. Phys. Chem., vol. 98, pp. 8627–31, 1994
Sullivan, G. R., Top. Stereochem., vol. 10, pp. 287–329, 1978
Suzuki, Electronic Absorption Spectra and Geometry of Organic Molecules, p. 102, 1967

What is claimed is:

1. A method for calculating a number representing an unknown enantiomeric composition of a chiral compound in an unknown sample, comprising:
    preparing a series of known samples, each of the known samples comprising a first complex, wherein, the first complex in each of the known samples comprises a ratio of a host compound and the chiral compound having a known enantiomeric composition,
        wherein, in each of the known samples, the ratio of the chiral compound to the host compound remains the same and the enantiomeric composition of the chiral compound is varied, and wherein, in each of the known samples, the concentrations of the chiral compound and of the host compound are at a preset level;
    collecting and storing spectral data of the known samples at various wavelengths;
    performing a principal component analysis to select a spectral range of wavelengths in which the spectral differences arising in each of the known samples due to an influence of the enantiomeric composition is most appreciable to give the selected range of wavelengths;
    performing a partial-least-squares regression of the spectral data over the selected range of wavelengths for each of the series of the known samples to determine a series of regression coefficients and a regression constant;

entering the series of regression coefficients for the selected range of wavelengths into a regression vector;

collecting and storing spectral data of the unknown sample at the selected range of wavelengths to give unknown spectral data, wherein the unknown sample comprises a second complex having the same ratio of the chiral compound to the host compound as that of the first complex in each of the known samples, and wherein, in the unknown sample, the concentrations of the chiral compound and of the host compound are at the preset level; and inserting the unknown spectral data into the regression vector to allow calculation of the number representing the unknown enantiomeric composition of the chiral compound in the unknown sample, wherein the number is useful for assessing enantiomeric purity of the unknown sample to evaluate its safety and efficacy in pharmaceutical applications.

2. The method of claim 1, wherein the regression vector is:

$$X_R = k_0 + k_1 A_1 + k_2 A_2 + \ldots + k_n A_n,$$

and wherein:

$X_R$ is the unknown enantiomeric composition of the chiral compound in the unknown sample, $k_i$ is the series of regression coefficients calculated for each of the wavelengths in the selected range of wavelengths, $A_i$ is the spectral data of the unknown compound at each of the wavelengths in the selected range of wavelengths, i is the selected range of wavelengths, 1–n, and $k_0$ is the regression constant.

3. The method of claim 1, wherein the host compound comprises a homochiral molecule capable of forming a diastereomeric compound or complex with the chiral compound.

4. The method of claim 1, wherein the host compound is selected from the group consisting of modified cyclodextrins, chiral crown ethers, chiral cryptands, chiral podands, chiral calixarenes, and naturally occurring homochiral molecules.

5. The method of claim 1, wherein the host compound is selected from the group consisting of α-cyclodextrin, β-cyclodextrin, and γ-cyclodextrin.

6. The method of claim 1, wherein the chiral compound comprises a compound capable of forming a complex with the host compound and having an absorption band in the selected range of wavelengths.

7. The method of claim 1, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

8. The method of claim 1, wherein the chiral compound is selected from the group consisting of ibuprofen, norephedrine, phenylglycine, tartaric acid, glycidyl butyrate, aspartic acid, phenylalanine, and arabinose.

9. The method of claim 1, wherein the spectral data is UV absorption spectral data, fluorescence emission spectral data, Raman spectral data, or NMR spectral data.

10. A method for calculating a number representing an unknown enantiomeric composition of a chiral compound in an unknown sample, comprising:

preparing a series of known samples, each of the known samples comprising a first complex, wherein, the first complex in each of the known samples comprises a ratio of α-cyclodextrin and the chiral compound having a known enantiomeric composition, wherein, in each of the known samples, the ratio of the chiral compound to α-cyclodextrin remains the same and the enantiomeric composition of the chiral compound is varied, and wherein, in each of the known samples, the concentrations of the chiral compound and of α-cyclodextrin are at the preset level;

collecting and storing spectral data of the first complex in each of the known samples at various wavelengths;

performing a principal component analysis to select a spectral range of wavelengths in which the spectral differences arising in each of the known samples due to an influence of the enantiomeric composition is most appreciable to give the selected range of wavelengths;

performing a partial-least-squares regression of the spectral data over the selected range of wavelengths for each of the series of the known samples to determine a series of regression coefficients and a regression constant;

entering the series of regression coefficients for the selected range of wavelengths into a regression vector having the formula:

$$X_R = k_0 + k_1 A_1 + k_2 A_2 + \ldots + k_n A_n,$$

wherein $X_R$ is the unknown enantiomeric composition of the chiral compound in the unknown sample, $k_i$ is the series of regression coefficients calculated for each of the wavelengths in the selected range of wavelengths, $A_i$ is the spectral data of the unknown compound at each of the wavelengths in the selected range of wavelengths, i is the selected range of wavelengths, 1–n, and $k_0$ is the regression constant;

collecting and storing spectral data of the chiral compound in the unknown sample to give unknown spectral data, wherein the unknown sample comprises a second complex having the same ratio of the chiral compound to α-cyclodextrin as that of the first complex in each of the known samples, and wherein, in the unknown sample, the concentrations of the chiral compound and of α-cyclodextrin are at the preset level; and inserting the unknown spectral data into the regression vector to allow calculation of the number representing the unknown enantiomeric composition of the chiral compound in the unknown sample, wherein the number is useful for assessing enantiomeric purity of the unknown sample to evaluate its safety and efficacy in pharmaceutical applications.

11. The method of claim 10, wherein the chiral compound comprises a compound capable of forming a complex with the host compound and having an absorption band in the selected range of wavelengths.

12. The method of claim 10, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

13. The method of claim 10, wherein the chiral compound is selected from the group consisting of ibuprofen, norephedrine, phenylglycine, tartaric acid, glycidyl butyrate, aspartic acid, phenylalanine, and arabinose.

14. The method of claim 10, wherein the spectral data is UV absorption spectral data, fluorescence emission spectral data, Raman spectral data, or NMR spectral data.

15. A method for calculating a number representing an unknown enantiomeric composition of a chiral compound in an unknown sample, comprising:

preparing a series of known samples, each of the known samples comprising a first complex, wherein, the first complex in each of the known samples comprises a ratio of β-cyclodextrin and the chiral compound having a known enantiomeric composition,
wherein in each of the known samples, the ratio of the chiral compound to β-cyclodextrin remains the same and the enantiomeric composition of the chiral compound is varied, and wherein, in each of the known samples, the concentrations of the chiral compound and of β-cyclodextrin are at a preset level;

collecting and storing spectral data of the first complex in each of the known samples at various wavelengths;

performing a principal component analysis to select a spectral range of wavelengths in which the spectral differences arising in each of the known samples due to an influence of the enantiomeric composition is most appreciable to give the selected range of wavelengths;

performing a partial-least-squares regression of the spectral data over the selected range of wavelengths for each of the series of the known samples to determine a series of regression coefficients and a regression constant;

entering the series of regression coefficients for the selected range of wavelengths into a regression vector having the formula:

$$X_R = k_0 + k_1 A_1 + k_2 A_2 + \ldots + k_n A_n,$$

wherein $X_R$ is the unknown enantiomeric composition of the chiral compound in the unknown sample, $k_i$ is the series of regression coefficients calculated for each of the wavelengths in the selected range of wavelengths, $A_i$ is the spectral data of the unknown compound at each of the wavelengths in the selected range of wavelengths, i is the selected range of wavelengths, 1–n, and $k_0$ is the regression constant;

collecting and storing spectral data of the chiral compound in the unknown sample to give unknown spectral data, wherein the unknown sample comprises a second complex having the same ratio of the chiral compound to β-cyclodextrin as that of the first complex in the known samples, and wherein, in the unknown sample, the concentrations of the chiral compound and of β-cyclodextrin are at the preset level; and inserting the unknown spectral data into the regression vector to allow calculation of the number representing the unknown enantiomeric composition of the chiral compound in the unknown sample, wherein the number is useful for assessing enantiomeric purity of the unknown sample to evaluate its safety and efficacy in pharmaceutical applications.

16. The method of claim 15, wherein the chiral compound comprises a compound capable of forming a complex with the host compound and having an absorption band in the selected range of wavelengths.

17. The method of claim 15, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

18. The method of claim 15, wherein the chiral compound is selected from the group consisting of ibuprofen, norephedrine, phenylglycine, tartaric acid, glycidyl butyrate, aspartic acid, phenylalanine, and arabinose.

19. The method of claim 15, wherein the spectral data is UV absorption spectral data, fluorescence emission spectral data, Raman spectral data, or NMR spectral data.

20. A method for calculating a number representing an unknown enantiomeric composition of a chiral compound in an unknown sample, comprising:

preparing a series of known samples, each of the known samples comprising a first complex, wherein, the first complex in each of the known samples comprises a ratio of γ-cyclodextrin and the chiral compound having a known enantiomeric composition,
wherein in each of the known samples, the ratio of the chiral compound to γ-cyclodextrin remains the same and the enantiomeric composition of the chiral compound is varied, and wherein, in each of the known samples, the concentrations of the chiral compound and of γ-cyclodextrin are at a preset level;

collecting and storing spectral data of the first complex in each of the known samples at various wavelengths;

performing a principal component analysis to select a spectral range of wavelengths in which the spectral differences arising in each of the known samples due to an influence of the enantiomeric composition is most appreciable to give the selected range of wavelengths;

performing a partial-least-squares regression of the spectral data over the selected range of wavelengths for each of the series of the known samples to determine a series of regression coefficients and a regression constant;

entering the series of regression coefficients for the selected range of wavelengths into a regression vector having the formula:

$$X_R = k_0 + k_1 A_1 + k_2 A_2 + \ldots + k_n A_n,$$

wherein $X_R$ is the unknown enantiomeric composition of the chiral compound in the unknown sample, $k_i$ is the series of regression coefficients calculated for each of the wavelengths in the selected range of wavelengths, $A_i$ is the spectral data of the unknown compound at each of the wavelengths in the selected range of wavelengths, i is the selected range of wavelengths, 1–n, and $k_0$ is the regression constant;

collecting and storing spectral data of the chiral compound in the unknown sample to give unknown spectral data, wherein the unknown sample comprises a second complex having the same ratio of the chiral compound to γ-cyclodextrin as that of the first complex in each of the known samples, and wherein, in the unknown sample, the concentrations of the chiral compound and of γ-cyclodextrin are at the preset level; and inserting the unknown spectral data into the regression vector to allow calculation of the number representing the unknown enantiomeric composition of the chiral compound in the unknown sample, wherein the number is useful for assessing enantiomeric purity of the unknown sample to evaluate its safety and efficacy in pharmaceutical applications.

21. The method of claim 20, wherein the chiral compound comprises a compound capable of forming a complex with the host compound and having an absorption band in the selected range of wavelengths.

22. The method of claim 20, wherein the chiral compound is selected from the group consisting of chiral alkanes, chiral alkenes, chiral aromatics, chiral amines, chiral alcohols, chiral carboxylic acids, chiral organo-halogens, chiral aldehydes, chiral ketones, chiral ethers, chiral aromatic amines, chiral aromatic alcohols, chiral aromatic acids, chiral heterocyclic compounds, chiral alkaloids, and compounds comprising combinations thereof.

23. The method of claim 20, wherein the chiral compound is selected from the group consisting of ibuprofen, norephedrine, phenylglycine, tartaric acid, glycidyl butyrate, aspartic acid, phenylalanine, and arabinose.

24. The method of claim 20, wherein the spectral data is UV absorption spectral data, fluorescence emission spectral data, Raman spectral data, or NMR spectral data.

* * * * *